(12) United States Patent
De Lera et al.

(10) Patent No.: US 6,534,545 B1
(45) Date of Patent: Mar. 18, 2003

(54) UNSATURATED DERIVATIVES AT THE 4-POSITION OF 6-TERT-BUTYL-1,1-DIMETHYLINDANE AND THEIR USE IN HUMAN AND VETERINARY MEDICINE AND COSMETICS

(75) Inventors: Angel De Lera, Vigo (ES); Beatriz Dominguez, Vigo (ES)

(73) Assignee: Galderma Research & Development, Valbonne (FR)

( * ) Notice: Subject to any disclaimer, the term of this patent is extended or adjusted under 35 U.S.C. 154(b) by 0 days.

(21) Appl. No.: 09/579,441

(22) Filed: May 26, 2000

Related U.S. Application Data

(63) Continuation-in-part of application No. 09/158,892, filed on Sep. 23, 1998.

(30) Foreign Application Priority Data

Sep. 25, 1997 (FR) ............................................. 97 11946

(51) Int. Cl.[7] ...................... A61K 31/19; C07D 323/02; C07D 295/00; C07D 471/02; C07H 17/06

(52) U.S. Cl. ...................... 514/570; 548/400; 548/100; 548/539; 549/429; 549/29; 549/20; 549/200; 562/405; 562/553; 562/571; 562/575; 544/106; 544/122; 544/169; 544/386; 546/122; 546/233; 546/184; 546/290; 424/78.23; 424/352; 536/13; 536/123

(58) Field of Search .......................... 549/20, 200, 29, 549/429; 548/400, 539, 100, 290; 514/570; 544/169, 106, 386, 122; 546/233, 184, 290; 424/78.23, 352; 536/123.13; 562/553, 571, 575

(56) References Cited

FOREIGN PATENT DOCUMENTS

| EP | 0 595 197 A1 | 5/1994 |
| FR | 2 390 428 | 5/1978 |
| FR | 2 601 670 | 7/1986 |

Primary Examiner—Alan L. Rotman
Assistant Examiner—Taylor V. Oh
(74) Attorney, Agent, or Firm—Nixon & Vanderhye P.C

(57) ABSTRACT

6-tert-Butyl-1,1-dimethylindane derivatives which are unsaturated in the 4-position of formula:

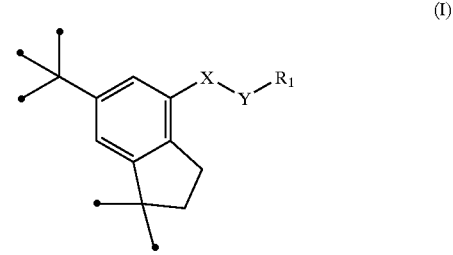

(I)

X represents:
(i) either a radical of formula: (a)

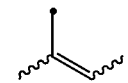

and Y represents a radical of formula: (b)

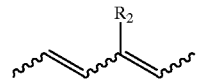

(ii) or a radical of formula: (c)

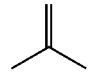

and Y represents either a radical of formula (b) or a radical of formula:

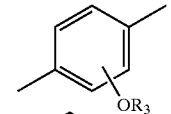

(d)

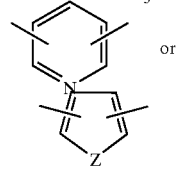

(e)
or
(f)

Z being —O—, —S— or

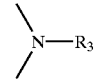

$R_1$ represents —$CH_3$, —$(CH_2)_p$—$OR_4$, —$(CH_2)_p$—$COR_5$ or —$S(O)_t$—$R_6$,
p being 0, 1, 2 or 3, t being 0, 1 or 2, $R_2$ represents H or lower alkyl, $R_3$ represents H, lower alkyl or —$COR_7$, $R_4$ represents H, lower alkyl, —$COR_7$, aryl, aralkyl, mono- or polyhydroxyalkyl, or a polyether radical, $R_5$ represents H, lower alkyl, —$OR_8$ or —N(r')(r"), $R_6$ represents H or lower alkyl, $R_7$ represents lower alkyl, $R_8$ represents H, alkyl, alkenyl, alkynyl, aryl, aralkyl, mono- or polyhydroxyalkyl, a sugar residue or an amino acid residue,
r' and r" represent H, lower alkyl, —$COR_7$, aryl, a sugar residue or an amino acid residue or r' and r" form a heterocycle, and the salts of the compounds of formula (I).

Use in the topical and systemic treatment of dermatological conditions, as well as in cosmetics.

21 Claims, No Drawings

UNSATURATED DERIVATIVES AT THE 4-POSITION OF 6-TERT-BUTYL-1,1-DIMETHYLINDANE AND THEIR USE IN HUMAN AND VETERINARY MEDICINE AND COSMETICS

This application is a continuation-in-part of Ser. No. 09/158,892, filed Sep. 23, 1998, which is based on FR 9711946, filed Sep. 25, 1997, the entire contents of each of which is incorporated herein by reference.

The subject-matter of the present invention is new unsaturated derivatives at the 4-position of 6-tert-butyl-1-1 dimethylindane, their process of preparation and their use in human or veterinary medicine and in cosmetics.

It is well known that all-trans-retinoic acid (AtRA) and certain synthetic analogues (retinoids) play a fundamental role in cell proliferation and differentiation. These pharmacological properties confer an advantage on retinoids in the treatment of dermatological conditions, such as acne or psoriasis. In addition, these compounds have applications in oncology in the treatment and prevention of certain cancers.

The compounds according to the invention, which are synthetic compounds also of the retinoid type, exhibit an activity in the fields of cell differentiation and proliferation. These compounds can consequently be used in the topical and systemic treatment of dermatological conditions linked to a disorder of keratinization, dermatological conditions (or others) having an inflammatory, viral and/or immunoallergic component, and dermal or epidermal proliferations, whether benign or malignant. These compounds can additionally be used in the treatment of degenerative diseases of the connective tissue, for controlling ageing of the skin, whether photoinduced or chronologic, and treating disorders of cicatrization. Finally, they find an application in the ophthalmological field, in particular in the treatment of corneopathies.

They can also be used in cosmetic compositions for body or hair hygiene.

The compounds according to the invention can be represented by the following general formula (I):

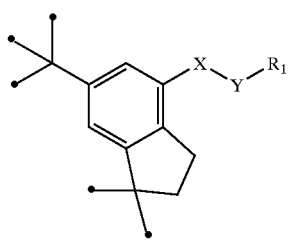

(I)

in which:

X represents:
(i) either a divalent radical of following formula:

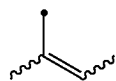

(a)

and Y then represents a divalent radical of following formula:

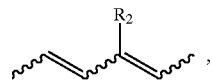

(b)

(ii) or a divalent radical of formula:

(c)

and Y then represents either a divalent radical corresponding to the divalent radical of formula (b) above or one of the divalent radicals of following formula:

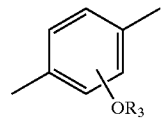

(d)

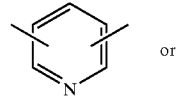

(e)

or

(f)

Z being —O—, —S— or

$R_1$ represents —$CH_3$, —$(CH_2)_p$—$OR_4$, —$(CH_2)_p$—$COR_5$ or —$S(O)_t$—$R_6$,
being 0, 1, 2 or 3,
being 0, 1 or 2,
$R_2$ represents H or lower alkyl,
$R_3$ represents H, lower alkoxy or —$OCOR_7$,
$R_4$ represents H, lower alkyl, —$COR_7$, aryl, aralkyl, mono- or polyhydroxyalkyl, or a polyether radical,
$R_5$ represents H, lower alkyl, —$OR_8$ or

$R_6$ represents H or lower alkyl,
$R_7$ represents lower alkyl,
$R_8$ represents H, alkyl, alkenyl, alkynyl, aryl, aralkyl, mono- or polyhydroxyalkyl, a sugar residue or an amino acid residue,
r' and r", identical or different, represent H, lower alkyl, —$COR_7$, aryl, a sugar residue or an amino acid residue or r' and r", taken together, form a heterocycle, and the salts of the compounds of formula (I), when $R_1$ represents a carboxylic acid group, and the geometrical and optical isomers of the compounds of formula (I).

When the compounds according to the invention are provided in the form of a salt, it is preferably a salt of an alkali metal or alkaline earth metal or alternatively of zinc or of an organic amine.

According to the invention, lower alkyl radical is understood to mean a linear or branched $C_1$–$C_6$ radical, preferably methyl, ethyl, propyl, isopropyl, tert-butyl and n-hexyl radicals.

Alkyl radical is understood to mean a linear or branched $C_1$–$C_{20}$ radical, preferably methyl, ethyl, isopropyl, butyl, tert-butyl, 2-ethylhexyl, octyl, dodecyl, hexadecyl and octadecyl radicals.

Lower alkoxy radical is understood to mean a radical having 1 to 6 carbon atoms, preferably methoxy, ethoxy, isopropoxy and butoxy radical.

Alkenyl radical is understood to mean a linear or branched radical preferably having from 2 to 5 carbon atoms and exhibiting one or two ethylenic unsaturation(s), such as the allyl radical.

Alkynyl radical is understood to mean a radical, having from 3 to 6 carbon atoms, comprising 1 or 2 triple bond(s), such as the 2-propynyl, 2-butynyl and 2,4-hexadiynyl radicals.

The radical of formula —$COR_7$ ($R_7$ being lower alkyl) or acyl radical is preferably selected from the acetyl, propionyl or pivaloyl radicals.

Monohydroxyalkyl radical is understood to mean a radical preferably having from 2 to 4 carbon atoms, preferably the 1-hydroxyethyl, 2-hydroxypropyl, 3-hydroxypropyl or 4-hydroxybutyl radicals.

Polyhydroxyalkyl radical is understood to mean a radical preferably having from 3 to 6 carbon atoms and from 2 to 5 hydroxyl groups, such as the 2,3-dihydroxy-propyl, 2,3,4-trihydroxybutyl or 2,3,4,5-tetrahydroxy-pentyl radicals or the pentaerythritol residue.

Polyether radical is understood to mean a radical having from 2 to 6 carbon atoms and from 1 to 3 oxygen or sulphur atoms, such as the methoxymethyl ether, methoxyethoxymethyl ether or methylthiomethyl ether radicals.

Aryl radical is understood to mean preferably the phenyl radical, optionally substituted by at least one halogen atom, such as Br, Cl or I, one hydroxyl group, one nitro group, one methoxy group or one optionally substituted amine group.

Aralkyl radical is understood to mean preferably the benzyl or phenethyl radical, optionally substituted by at least one halogen atom as defined above, one hydroxyl group, one nitro group or one methoxy group.

Amino acid residue is understood to mean in particular a residue deriving from lysine, glycine or aspartic acid.

Sugar residue is understood to mean a residue deriving from glucose, galactose or mannose or alternatively glucuronic acid.

Heterocycle is understood to mean preferably a piperidino, morpholino, pyrrolidino or piperazino radical, the latter being optionally substituted in the 4-position by a lower $C_1$–$C_6$ alkyl or a mono- or poly-hydroxyalkyl as defined above.

According to a first preferred embodiment, the compounds according to the invention correspond to the following general formula:

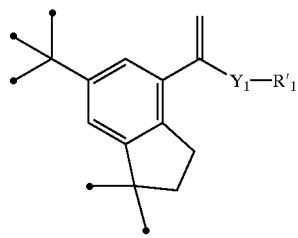

(II)

in which:

$Y_1$ represents one of the divalent radicals of formula:

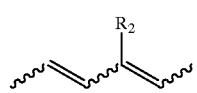

(b)

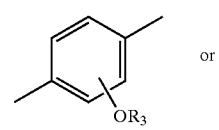

or (d)

(f)

$R_2$, $R_3$ and Z having the same meanings as those given for the formula (I) above, $R'_1$ represents —$(CH_2)_{p'}$—$COOR'_8$, p' being 0 and $R'_8$ representing H or lower alkyl.

According to a second preferred embodiment, the compounds according to the invention correspond to the following general formula:

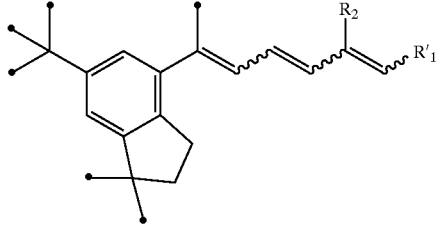

(III)

in which:

$R_2$ represents H or lower alkyl, and $R'_1$ represents —$(CH_2)_{p'}$—$COOR'_8$, p' being 0 and $R'_8$ being H or lower alkyl.

Among the compounds corresponding to the above formulae (I), (II) and (III), mention may be made of the following examples:

methyl (2E,4E)-6-[4-(6-tert-butyl-1,1-dimethylindanyl)]-3-methylhepta-2,4,6-trienoate, (2E,4E)-6-[4-(6-tert-butyl-1,1-dimethylindanyl)]-3-methylhepta-2,4,6-trienoic acid, methyl (2E,4E)-6-[4-(6-tert-butyl-1,1-dimethylindanyl)]hepta-2,4,6-trienoate, (2E,4E)-6-[4-(6-tert-butyl-1,1-dimethylindanyl)]hepta-2,4,6-trienoic acid, methyl (2E,4E,6E)-7-[4-(6-tert-butyl-1,1-dimethylindanyl)]-3,7-dimethylhepta-2,4,6-trienoate, (2E,4E,6E)-7-[4-(6-tert-butyl-1,1-dimethylindanyl)]-3,7-dimethylhepta-2,4,6-trienoic acid,
methyl (2E,4E,6E)-7-[4-(6-tert-butyl-1,1-dimethylindanyl)]-7-methylhepta-2,4,6-trienoate,
(2E,4E,6E)-7-[4-(6-tert-butyl-1,1-dimethylindanyl)]-7-methylhepta-2,4,6-trienoic acid,
ethyl 4-[1-[4-(6-tert-butyl-1,1-dimethylindanyl)]ethenyl]benzoate,
4-[1-[4-(6-tert-butyl-1,1-dimethylindanyl)]ethenyl]benzoic acid,
3-[1-(6-tert-butyl-1,1-dimethylindan-4-yl)ethen-1-yl]-thiophene-2-carboxylic acid,
3-[1-(6-tert-butyl-1,1-dimethylindan-4-yl)ethen-1-yl]-thiophene-2-carboxaldehyde,
2-[1-(6-tert-butyl-1,1-dimethylindan-4-yl)ethen-1-yl]-thiophene-3-carboxaldehyde,
2-[1-(6-tert-butyl-1,1-dimethylindan-4-yl)ethen-1-yl]-thiophene-3-carboxylic acid,
Methyl 6-[(6-tert-butyl-1,1-dimethylindan-4-yl)ethen-1-yl]-3-pyridinecarboxylate,
6-[(6-tert-butyl-1,1-dimethylindan-4-yl)ethen-1-yl]-3-pyridinecarboxylic acid.

The present invention is also directed to the process for the preparation of the compounds of formula (I) according to the reaction schemes of Tables A and B.

With reference to Table A, 4-acetyl-6-tert-butyl-1,1-dimethylindane (1) is converted into the intermediate 6-tert-butyl-4-ethenyl-1,1-dimethylindane by treatment with lithium diisopropylamide (LDA) and is then treated with an alkyl chlorophosphate, such as diethyl chlorophosphate. The resulting mixed phosphate intermediate is subsequently again treated with LDA and thus results in the 6-tert-butyl-4-ethynyl-1,1-dimethylindane (2).

The latter can then be converted to the vinyl iodide (3) by the action of trimethylsilyl iodide or chloride or be converted to the propylene iodide (4) by a methylalumination mediated by a zirconium complex (bis(cyclopentadienyl) zirconium dichloride complex), followed by an exchange between aluminium and iodine according to the conditions described by A. Tollado et al., Tetrahedron, 1995, vol. 5, pages 2435–2454.

The iodinated derivatives (3) and (4) are subsequently used in a crosscoupling reaction with a polyenic organostannic compound of formula (5), catalysed by palladium (tris (dibenzylideneacetone)palladium complex), in order to result in the compounds of the formulae (Ia) and (Ib). The organostannic compound (5) can be replaced by a polyenic boronic acid and, in this case, the reaction is carried out under the crosscoupling conditions of the Suzuki type, modified by Kishi. According to these conditions, the mixture contains thallium hydroxide and the catalyst is Pd(PPh$_3$)$_4$, these conditions being described in detail in Synthesis, 1995, No. 3, p. 285.

With reference now to Table B, the compounds of formula (Ic) can be obtained from the vinyl iodide (3) of Table A by condensation with an arylboronic derivative (6) in the presence of tetrakis(triphenylphosphine)-palladium according to conditions described above in Synthesis.

When R$_1$ represents —COOH in the compounds according to the invention, these compounds are prepared by protecting the carboxylic acid group with a protective group of alkyl, allyl or tert-butyl type.

Conversion to the free form can be carried out:
in the case of an alkyl protective group, by means of sodium hydroxide or lithium hydroxide in an alcoholic solvent, such as methanol, or in THF;
in the case of an allyl protective group, by means of a catalyst, such as certain transition metal complexes, in the presence of a secondary amine, such as morpholine;
in the case of a protective group of tert-butyl type, by means of trimethylsilyl iodide.

When R$_1$ represents —OH in the compounds according to the invention, these compounds can be obtained from the corresponding acid by reduction in the presence of lithium aluminium hydride.

When R$_1$ represents

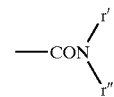

the compounds can be obtained by conversion of the corresponding acid to the acid chloride, for example with thionyl chloride, and then reaction with ammonia or an appropriate amine.

The compounds according to the invention bind to RXR receptors and have an agonist activity with respect to these receptors.

The binding and transactivation properties as RXR agonists are determined by known methods, such as, for example, according to Levin et al., Nature, 1992, 355, 359–361; Allenby et al., Proc. Natl. Acad. Sci., 1993, 90, 30–4; Allenby et al., J. Biol. Chem., 1994, 269, 16689–16695.

The RXR agonist activity is also determined by the test as disclosed in EP-A-749,752. This test comprises the following steps:

(i) a sufficient amount of a compound which is an active ligand of at least one receptor of the superfamily of steroid/thyroid nuclear receptors, other than a ligand specific for RXR receptors, and which can heterodimerize with the RXRs, such as, for example, an RAR agonist molecule, is applied topically to a portion of the skin of a mammal, (ii) a molecule capable of exhibiting an agonist activity with respect to RXRs is administered systemically or topically to the same portion of the skin of a mammal, before, during or after the steps (i), (iii) the pharmacological response over the portion of the skin, thus treated, of the mammal is then evaluated. This response consists of a thickening of the ear. Thus, the response of a topical application to the ear of a mammal of an RAR agonist will be potentiated by topical or systemic administration of an agonist for RXR receptors.

The present invention is also directed to the above compounds of formula (I) as medicament.

The compounds according to the invention are particularly well suited to the following fields of treatment:

1) For treating dermatological conditions linked to a disorder of keratinization involving differentiation and proliferation, in particular for treating acne vulgaris, comedonic or polymorphic acne, acne rosacea, nodulocystic acne, acne conglobata, senile acne and secondary acnes such as solar, drug-induced or occupational acne, 2) For treating other types of disorders of keratinization, in particular ichthyoses, ichthyosiform conditions, Darier's disease, palmoplantar keratoderma; leucoplakia and leucoplakiform conditions or cutaneous or mucosal (oral) lichen, 3) For treating other dermatological conditions linked to a disorder of keratinization with an inflammatory and/or immunoallergic component and, in particular, all forms of psoriasis, either cutaneous, mucosal or ungual, and even psoriatic rheumatism, or alternatively cutaneous atopy, such as eczema, or respiratory atopy or alternatively gingival hypertrophy; the compounds can also be used in certain inflammatory conditions which do not show disorders of keratinization, 4) For treating all dermal or epidermal proliferations, whether they are benign or malignant and whether they are or are not of viral origin, such as common warts, flat warts and epidermodysplasia verruciformis, florid or oral papillomatoses and the proliferations which can be induced by ultraviolet radiation, in particular in the case of basal cell and prickle cell epithelioma, 5) For treating other dermatological disorders, such as bullous dermatoses and collagen diseases, 6) For treating certain ophthalmological disorders, in particular corneopathies, 7) For repairing or controlling ageing of the skin, whether photoinduced or chronologic, or for reducing actinic keratoses and pigmentations or any pathology associated with chronologic or actinic ageing, 8) For preventing or treating the stigmata of epidermal and/or dermal atrophy induced by local or systemic corticosteroids, or any other form of cutaneous atrophy, 9) For preventing or treating disorders of cicatrization or for preventing or repairing stretch marks, 10) For controlling disorders of the sebaceous function such as hyperseborrhoea of acne or simple seborrhoea, 11) In the treatment or prevention of cancerous or pre-cancerous conditions, 12) In the treatment of inflammatory conditions such as arthritis, 13) In the treatment of any condition of viral origin at the cutaneous or general level, 14) In the prevention or treatment of alopecia, 15) In the treatment of dermatological or general conditions with an immunological component, 16) In the treatment of ailments of the cardiovascular system such as arteriosclerosis, hypertension, non-insulin-dependent diabetes and obesity.

In the therapeutic fields mentioned above, the compounds according to the invention can advantageously be employed in combination with other known retinoids, with vitamins D or their derivatives, with corticosteroids or oestrogens, or employed in combination with compounds which control free radicals, with α-hydroxy or α-keto acids or their derivatives, or alternatively with potassium-channel blockers.

Vitamins D or their derivatives is understood to mean, for example, the derivatives of vitamin $D_2$ or $D_3$ and in particular 1,25-dihydroxyvitamin $D_3$.

Compounds which control free radicals is understood to mean, for example, α-tocopherol, superoxide dismutase (SOD), ubiquinol or certain metal-chelating agents.

α-Hydroxy or α-keto acids or their derivatives is understood to mean, for example, lactic, malic, citric, glycolic, mandelic, tartaric, glyceric or ascorbic acids and salicylic acid derivatives or their salts, amides or esters.

Potassium-channel blockers is understood to mean, for example, minoxidil (2,4-diamino-6-piperidinopyrimidine 3-oxide) and its derivatives.

It is also a subject-matter of the present invention a medicinal composition comprising at least one compound of formula (I) as defined hereinabove, one of its optical or geometrical isomers or one of its salts.

The medicinal compositions are more particularly intended especially for treating the abovementioned conditions and are characterized in that they comprise, in a pharmaceutically acceptable vehicle, at least one compound of formula (I), one of its optical or geometrical isomers or one of its salts.

The administration of the compounds according to the invention can be carried out enterally, parenterally, topically or ocularly.

For enteral administration, the medicaments can be provided in the form of tablets, hard gelatin capsules, dragées, syrups, suspensions, solutions, powders, granules, emulsions or polymeric or lipid vesicles or nanospheres or microspheres which make possible controlled release. For parenteral administration, the compositions can be provided in the form of solutions or suspensions for infusion or for injection.

The compounds according to the invention are generally administered at a daily dose of approximately 0.01 mg/kg to 100 mg/kg by body weight in 1 to 3 intakes.

The topical pharmaceutical compositions containing the compounds according to the invention are intended for treating the skin and the mucosal membranes and are provided in the form of ointments, creams, milks, salves, powders, impregnated pads, solutions, gels, sprays, lotions or suspensions. They can also be provided in the form of polymeric or lipid vesicles or nanospheres or microspheres or of polymeric patches and of hydrogels which make possible controlled release. These compositions for topical administration can be provided either in anhydrous form or in aqueous form, according to the clinical indication.

For ocular administration, they are mainly eye washes.

The compositions for topical or ocular administration contain at least one compound of formula (I) as defined above, one of its optical or geometrical isomers or one of its salts, at a concentration preferably of between 0.001 and 5% with respect to the total weight of the composition.

The compounds of formula (I) according to the invention also find an application in the cosmetics field, in particular in body and hair hygiene, and especially for the treatment of skin with a tendency to develop acne, for hair regrowth and combating hair loss, for combating the greasy appearance of the skin or the hair, in protecting against the deleterious effects of sunlight or in the treatment of physiologically dry skin, and for preventing and/or for controlling photoinduced or chronologic ageing.

In the cosmetics field, just as in the therapeutic field, the compounds according to the invention can advantageously be employed in combination with other known retinoids, with vitamins D or their derivatives, or with corticosteroids, or alternatively in combination with compounds which control free radicals, with α-hydroxy or α-keto acids or their derivatives, or alternatively with potassium-channel blockers.

The cosmetic compositions according to the present invention comprise, in a cosmetically acceptable vehicle, at least one compound of formula (I), one of its optical or geometrical isomers or one of its salts, these compositions being provided in particular in the form of a cream, a milk, a lotion, a gel, polymeric or lipid vesicles or nanospheres or microspheres, a soap or a shampoo.

The concentration of compound of formula (I) in the cosmetic compositions is preferably between 0.001 and 3% by weight.

The pharmaceutical and cosmetic compositions according to the invention can additionally contain inert or even pharmacodynamically or cosmetically active additives or combinations of these additives and especially: wetting agents; depigmenting agents such as hydroquinone, azelaic acid, caffeic acid or kojic acid; emollients; hydrating agents such as glycerol, polyethylene glycol 400, thiamorpholinone and its derivatives or urea; anti-seborrhoeic or anti-acne agents such as S-carboxymethylcysteine, S-benzylcysteamine, their salts and their derivatives, or benzoyl peroxide; antibiotics such as erythromycin and its esters, neomycin, clindamycin and its esters, or tetracyclins; antifungal agents such as ketoconazole or 4,5-polymethylene-3-isothiazolinones; agents promoting hair regrowth, such as minoxidil (2,4-diamino-6-piperidinopyrimidine 3-oxide) and its derivatives, diazoxide (7-chloro-3-methyl-1,2,4-benzothiadiazine 1,1-dioxide) and phenytoin(5,4-diphenylimidazolidine-2,4-dione); non-steroidal anti-inflammatory agents; carotenoids and especially β-carotene; anti-psoriatic agents such as anthralin and its derivatives; and finally eicosa-5,8,11,14-tetraynoic and eicosa-5,8,11-triynoic acids, their esters and amides.

The compositions according to the invention can also contain flavour enhancers, preserving agents such as the esters of para-hydroxybenzoic acid, stabilizing agents, moisture-regulating agents, pH-regulating agents, osmotic-pressure-modifying agents, emulsifying agents, UV-A and UV-B screening agents and antioxidants such as α-tocopherol, butylated hydroxyanisole or butylated hydroxytoluene.

A number of examples of the preparation of active compounds of formula (I) according to the invention, as well as formulation examples comprising them, will now be given by way of illustration.

EXAMPLES

Example 1

Methyl (2E,4E)-6-[4-(6-tert-butyl-1,1-dimethyl-indanly)]-3-methylhepta-2,4,6-trienoate (a) (2E,4E)-5-(tri-n-butylstannyl)-3-methylpenta-2,4-dien-1-ol CuCN (2.01 g, 22.40 mmol) is introduced into a round-bottomed flask placed under argon, THF (60 ml) is then added and the mixture is cooled to −78° C. n-Butyl-lithium (1.6 M, 27.7 ml, 44.40 mmol) is then added drop-wise and the mixture is allowed to slowly return to room temperature. It is again cooled to −78° C. and n-Bu$_3$SnH (12 ml, 44.40 mmol) is added and the mixture is stirred for 10 minutes, during which the hydrogen is discharged. (2E)-3-Methylpent-2-en-4-yn-1-ol (1.86 g, 19.31 mmol) is then added, the reaction mixture is left stirring for 45 minutes and then poured into 200 ml of an NH$_4$OH/NH$_4$Cl (10/90) solution. Extraction is carried out with ether (3×100 ml), drying is carried out over Na$_2$SO$_4$ and evaporation is carried out under vacuum.

After silica chromatography, elution being carried out with a hexane/ethyl acetate/triethylamine (89/10/1) mixture, 6.28 g (84%) of the expected compound are obtained in the form of an oil.

$^1$H NMR (250.13 MHz, CDCl$_3$) δ 0.9–1.2 (m, 15H, n-Bu), 1.3–1.5 (m, 6H, n-Bu), 1.5–1.7 (m, 6H, n-Bu), 1.78 (s, 3H, CH$_3$), 4.30 (t, J=6.2 Hz, 2H, 2H$_1$), 5.64 (t, J=6.2 Hz, 1H, H$_2$), 6.25 (d, J=19.3 Hz, $^2$J$_{Sn-H}$=68.0 Hz, 1H, H$_5$), 6.56 (d, J=19.3 Hz, $^3$J$_{Sn-H}$=63.0 Hz, 1H, H$_4$) ppm;

$^{13}$C NMR (75.5 MHz, CDCl$_3$) δ 9.9 (t, $^1$J$_{Sn-C}$=343.9/328.9 Hz, 3x), 12.3 (q, 3x), 14.1 (q), 27.7 (t, $^2$J$_{Sn-C}$=54.3 Hz, 3x), 29.5 (t, $^3$J$_{Sn-C}$=20.5 Hz, 3x), 59.9 (t), 128.7 (d, $^1$J$_{Sn-C}$=383.5/356.9 Hz, C$_5$), 130.2 (d, $^2$J$_{Sn-C}$=139.6 Hz, C$_4$), 138.1 (s, $^3$J$_{Sn-C}$=65.1 Hz, C$_3$), 150.4 (d) ppm;

MS (EI$^+$) m/e (relative intensity) 386 (M$^+$, 0.4), 335 (17), 333 (15), 332 (16), 331 ([M-Bu+1]$^+$, 100), 330 (36), 329 (75), 328 (28), 327 (42), 279 (17), 275 (98), 274 (33), 273 (74), 272 (27), 271 (43), 219 (86), 218 (27), 217 (69), 216 (24), 215 (42), 179 (18), 177 (27), 175 (21), 137 (63), 136 (17), 135 (50), 134 (6), 133 (30), 121 (42), 120 (21), 119 (33), 118 (16), 117 (19), 81 (25), 79 (25), 77 (16);

HRMS (EI$^+$) calc.: for C$_{18}$H$_{36}$OSn 386.1782, found: 386.1788;

FTIR ν 3800–3600 (br, —OH), 2962 (s, C—H), 2928 (S, C—H), 2857 (s), 1567 (m), 1460 (s, C—O), 1380 (w), 1184 (m) 1078 (m), 992 (s) cm$^{-1}$.

(b) (2E,4E)-5-(tri-n-butylstannyl)-3-methylpenta-2,4-dien-1-al

The sulphur trioxide-pyridine complex (477 mg, 3.00 mmol) is added to a cooled solution (−10° C.) of the compound obtained in 1a above (387 mg, 1.00 mmol) and triethylamine (0.42 ml, 3.00 mmol) in dichloromethane (3.3 ml). The mixture is stirred vigorously for 30 minutes at 0° C. and is then poured into an aqueous sodium chloride solution (10 ml, 1:1), and extraction is then carried out with ethyl ether (2×6 ml). The organic phases are washed with a 10% aqueous citric acid solution (4 ml) and a cold sodium chloride solution (2×4 ml). Separation is carried out by settling and the organic phases are subsequently dried over MgSO$_4$ and evaporated. The residue is purified by reverse phase HPLC (CH$_3$CN), in order to result in 371 mg (96%) of the expected compound in the form of an oil.

$^1$H NMR (250.13 MHz, CDCl$_3$) δ 0.8–1.1 (m, 15H, n-Bu), 1.2–1.4 (m, 6H, n-Bu), 1.4–1.6 (m, 6H, n-Bu), 2.24 (s, 3H, CH$_3$), 5.90 (d, J=8.2 Hz, 1H, H$_2$), 6.67 (d, J=19.3 Hz, $^3$J$_{Sn-H}$=57.7 Hz, 1H, H$_4$), 7.02 (d, J=19.3 Hz, $^2$J$_{Sn-H}$=59.0 Hz, 1H, H$_5$), 10.14 (d, J=8.2 Hz, 1H, CHO) ppm;

$^{13}$C NMR (75.5 MHz, CDCl$_3$) δ 10.1 (t, $^1$J$_{Sn-C}$=347.8/333.2 Hz, 3x), 12.8 (q), 14.0 (q, 3x), 27.6 (t, $^2$J$_{Sn-C}$=55.1 Hz, 3x), 29.4 (t, $^3$J$_{Sn-C}$=21.1 Hz, 3x), 129.5 (d), 142.0 (d, $^1$J$_{Sn-C}$=336.3 Hz, C$_5$), 149.1 (d), 154.8 (s), 192.6 (d, CHO) ppm;

MS (EI$^+$) m/e (relative intensity) 329 ([M-Bu+1]$^+$, 85), 328 (31), 327 (62), 326 (24), 325 (36), 273 (44), 272 (15), 271 (33), 269 (20), 17 (71), 216 (25), 215 (58), 213 (35), 137 (29), 135 (25), 95 ([M-SnBu$_3$]$^+$, 100);

HRMS (EI$^+$) calc.: for C$_{18}$H$_{34}$OSn 386.1632, found: 386.16–18;

FTIR (CHCl$_3$) ν 2966 (s, C—H), 2922 (s, C—H), 2857 (s, C—H), 1668 (s, C=O), 1600 (w, C=C), 1453 (w), 1197 (m), 1113 (m), 991 (m), 870 (m), 687 (m) cm$^{-1}$.

(c) methyl (2E,4E)-5-(tri-n-butylstannyl)-3-methyl1enta-2,4-dienoate

A mixture of KCN (0.31 g, 4.82 mmol) and MnO$_2$ (1.67 g, 19.26 mmol) is added to a cold solution (0° C.) of the aldehyde obtained in 1b above (0.37 g, 0.96 mmol) in methanol (4.8 ml). The resulting mixture is stirred at 0° C. for 90 minutes and filtered through celite. After removing the solvent, the residue is purified by silica chromatography, elution being carried out with a hexane/ethyl acetate (95/5) mixture, in order to result in 327 mg (82%) of the expected compound in the form of an oil.

$^1$H NMR (250.13 MHz, CDCl$_3$) δ 0.8–0.9 (m, 15H, n-Bu), 1.2–1.3 (m, 6H, n-Bu), 1.4–1.5 (m, 6H, n-Bu), 2.25 (d, J=1.1 Hz, 3H, CH$_3$), 3.71 (s, 3H, CO$_2$CH$_3$), 5.74 (br s, 1H, H$_2$), 6.56 (d, J=19.4 Hz, $^3$J$_{Sn-H}$=46.2 Hz, 1H, H$_4$), 6.80 (d, J=19.4 Hz, $^2$J$_{Sn-H}$=51.3 Hz, 1H, H$_5$) ppm;, $^{13}$C NMR (75.5 MHz, CDCl$_3$) δ 10.0 (t, $^1$J$_{Sn-C}$=346.5/331.1 Hz, 3x), 13.5 (q), 14.0 (q, 3x), 27.6 (t, $^2$J$_{Sn-C}$=54.6 Hz, 3x), 29.4 (t, $^3$J$_{Sn-C}$=20.8 Hz, 3x), 51.4 (q, CO$_2$CH$_3$), 118.6 (d), 138.4 (d, $^1$J$_{Sn-C}$=352.6/337.5 Hz, C$_5$), 149.4 (d, $^4$J$_{Sn-C}$=

10.9 Hz, $C_5$), 153.3 (s, $^3J_{Sn-C}$=62.5 Hz, $C_3$), 168.0 (s, $CO_2CH_3$) ppm;

MS (EI$^+$) m/e (relative intensity) 359 ([M-Bu+1]$^+$, 75), 358 (28), 357 (56), 356 (22), 355 (32), 303 (81), 302 (28), 301 (60), 300 (23), 299 (35), 251 (18), 250 (15), 247 (100), 246 (32), 245 (77), 244 (28), 243 (46), 151 (62), 150 (16), 149 (46), 148 (14);

HRMS (EI$^+$) calc.: for $C_{19}H_{36}O_2Sn$ 416.1737, found: 416.1726;

FTIR (CHCl$_3$) v 2955 (m, C—H), 2926 (m, C—H), 2852 (w, C—H), 1717 (s, C=O), 1615 (w, C=C), 1558 (w), 1435 (w) 1232 (m), 1152 (s) cm$^{-1}$.

(d) 6-tert-butyl-4-ethynyl-1,1-dimethylindane

Lithium diisopropylamide (LDA) is prepared by adding butyllithium (1.6 M in hexane, 16.11 ml, 25.78 mmol) to a solution of diisopropylamine (3.6 ml, 25.78 mmol) in THF (24 ml) at 0° C. The mixture is stirred for 30 minutes at this temperature and is then cooled to −78° C. 4-Acetyl-6-tert-butyl-1,1-dimethylindane (6.0 g, 24.55 mmol) is then slowly added. After stirring for 1 hour at −78° C., diethyl chlorophosphate (3.72 ml, 25.78 mmol) is added and the reaction mixture is allowed to return to room temperature over a period of 2–3 hours (mixture A).

LDA is prepared separately from diisopropylamine (7.74 ml, 55.24 mmol) and butyllithium (1.6 M in hexane, 34.52 ml, 55.24 mmol) in THF (95 ml) at 0° C. After stirring for 30 minutes and cooling to −78° C., the above mixture A, cooled beforehand to −78° C., is added thereto. The resulting reaction mixture is allowed to return to ambient temperature under stirring over a period of 2–3 hours and is then treated with water at 0° C. Extraction is carried out with hexane (3×50 ml), washing is carried out with ice-cold 1N HCl (100 ml) and a saturated NaHCO$_3$ solution (100 ml), and then drying over MgSO$_4$ and evaporation are carried out.

The residue is purified by silica chromatography, elution being carried out with hexane, in order to result in 4.89 g (88%) of the expected compound in the form of a white solid.

$^1$H NMR (250.13 MHz, CDCl$_3$) δ 1.26 (d, J=0.9 Hz, 6H, 2×CH$_3$), 1.32 (d, J=1.0 Hz, 9H, t-Bu), 1.95 (dt, J=7.2 and 0.9 Hz, 2H, 2H$_2$), 2.95 (t, J=7.2 Hz, 2H, 2H$_3$), 3.17 (s, 1H, H$_{2'}$), 7.15 (s, 1H, Ar—H), 7.33 (br s, 1H, Ar—H) ppm;

$^{13}$C NMR (62.89 MHz, CDCl$_3$) δ 28.6 (q), 29.1 (t), 31.4 (q), 34.6 (s), 41.0 (t), 44.5 (s), 78.9 (s), 83.0 (d), 117.6 (s), 119.8 (d), 127.1 (d), 143.1 (s), 149.9 (s), 152.6 (s) ppm;

MS (EI$^+$) m/e (relative intensity) 226 (M$^+$, 22), 212 (18), 211 ([M-CH$_3$]$^+$, 100), 165 (8), 155 (16), 153 (8), 152 (7), 58 (37), 57 (10);

HRMS (EI$^+$) calc.: for $C_{17}H_{22}$ 226.1723, found: 226.1721;

FTIR (CDCl$_3$) v 3290 (m, ≡C—H), 2954 (s, C—H), 2864 (m, C—H), 2103 (w, C≡C), 1580 (w), 1463 (m), 1362 (m), 1316 (w), 1253 (w), 878 (m), 650 (m) cm$^{-1}$.

(e) 6-tert-butyl-4-(1-iodoethen-1-yl)-1,1-dimethylindane

A solution of Me$_3$SiCl (1.04 ml, 8.30 mmol) in water (0.07 ml) is added fractionwise to a solution of sodium iodide (1.24 g, 8.30 mmol) in acetonitrile (23 ml). After 10 minutes, the alkyne obtained in 1d above (1.50 g, 6.64 mmol) is then added to this first solution and the mixture is stirred for 3 hours. 10 ml of water are subsequently added, extraction is carried out with ether (3×50 ml) and then the extracts are dried over MgSO$_4$.

After evaporation, the residue is purified by flash chromatography (SiO$_2$, hexane), in order to result in 2.29 g (97%) of the expected compound in the form of an oil.

$^1$H NMR (300.13 MHz, CDCl$_3$) δ 1.27 (s, 6H, 2×CH$_3$), 1.34 (s, 9H, t-Bu), 1.93 (t, J=7.2 Hz, 2H, H$_3$), 2.88 (t, J=7.2 Hz, 2H, H$_2$), 6.15 (d, J=1.2 Hz, 1H, H$_{2'}$), 6.18 (d, J=1.2 Hz, H$_{2'}$), 7.10 (br s, 1H, Ar—H), 7.18 (br s, 1H, Ar—H) ppm;

$^{13}$C NMR (75.47 MHz, CDCl$_3$) δ 29.1 (q, 2×), 29.7 (t), 32.0 (q, 3×), 35.2 (s), 41.9 (t), 44.5 (s), 105.8, 119.7 (d), 124.6 (d), 129.5 (t), 137.2 (s), 139.3 (s), 150.3 (s), 153.3 (s) ppm;

MS (EI$^+$) m/e (relative intensity) 354 (M$^+$, 3), 243 (2), 227 ([M-I]$^+$, 100), 212 (6), 197 (6), 165 (7), 155 (10), 153 (8), 152 (7), 141 (8), 129 (6), 128 (8), 127 (4), 115 (8), 57 (32);

HRMS (EI$^+$) calc.: for $C_{17}H_{23}I$ 354.0845, found: 354.0844;

FTIR (CHCl$_3$) v 2953 (s, C—H), 2862 (s, C—H), 1598 (m, C=C), 1476 (m), 1460 (m), 1361 (m), 1252 (w), 1202 (w) 896 (m), 878 (m), 656 (w), 643 (w) cm$^{-1}$.

(f) methyl (2E,4E)-6-[4-(6-tert-butyl-1,1-dimethyl-indanyl)]-3-methylhepta-2,4,6-trienoate Triphenylarsine (AsPh$_3$) (1.4 mg, 0.005 mmol) and Pd$_2$(dba)$_3$ (Tris(dibenzylideneacetone)polladium complex) (4.1 mg, 0.005 mmol) are added to a solution of the iodinated derivative obtained in 1e above (53 mg, 0.150 mmol) in anhydrous N-methylmorpholine (NMP) (2.1 ml). After 10 minutes, a solution of stannate obtained in 1c above (68 mg, 0.165 mmol) in NMP (1 ml) is added and the solution is stirred at 80° C. for 90 minutes. After addition of 2 ml of a saturated aqueous KF solution, the mixture is extracted with ether (3×5 ml). The organic extracts are washed with H$_2$O (3×5 ml) and are then dried over MgSO$_4$ and evaporated. The residue is then purified by silica chromatography, elution being carried out with a hexane/ethyl acetate (95/5) mixture, in order to result in 40 mg (76%) of a yellow solid.

$^1$H NMR (250.13 MHz, CDCl$_3$) δ 1.29 (s, 6H, 2×CH$_3$), 1.35 (s, 9H, t-Bu), 1.88 (t, J=7.1 Hz, 2H, 2H$_{2'}$), 2.36 (d, J=1.0 Hz, 3H, CH$_3$), 2.67 (t, J=7.1 Hz, 2H, 2H$_{3'}$), 3.69 (s, 3H, CO$_2$CH$_3$), 5.27 (d, J=1.7 Hz, 1H, H$_2$), 5.53 (s, 1H, H$_7$), 5.67 (s, 1H, H$_7$), 5.93 (d, J=15.8 Hz, 1H, H$_5$), 6.83 (d, J=15.8 Hz, 1H, H$_4$), 7.01 (d, J=1.7 Hz, 1H, Ar—H), 7.15 (d, J=1.7 Hz, 1H, Ar—H) ppm;

$^{13}$C NMR (62.89 MHz, CDCl$_3$) δ 13.7 (q), 28.6 (q, 2×), 28.8 (t), 31.6 (q, t-Bu), 34.6 (s), 41.5 (t), 44.1 (s), 50.9 (q), 118.1 (d), 119.4 (d), 120.6 (t), 124.0 (d), 134.9 (d), 135.2 (s), 135.9 (d), 137.9 (s), 147.8 (s), 149.8 (S), 152.5 (s), 152.6 (s), 167.4 (s) ppm;

MS (EI$^+$) m/e (relative intensity) 352 (M$^+$, 100), 337 ([M—CH$_3$]$^+$, 23), 277 (46), 249 (45), 221 (32), 181 (45), 165 (33), 58 (57), 57 (78);

HRMS (EI$^+$) calc.: for $C_{24}H_{32}O_2$ 352.2404, found: 352.2398;

FTIR (CHCl$_3$) v 2954 (s, C—H), 2871 (m, C—H), 1718 (s, C=O), 1624 (m, C=C), 1451 (m), 1373 (w), 1214 (m), 1155 (s), 1048 (m), 879 (w), 751 (m).

Example 2

(2E,4E)-6-[4-(6-tert-Butyl-1,1-dimethyl-indanyl)]-3-methylhepta-2,4,6-trienoic acid The stannic derivative obtained in Example 1 (1c) (100 mg, 0.241 mmol) in 0.5 ml of ether is added dropwise with stirring to a solution of KOSiMe$_3$ (90%, 34 mg, 0.241 mmol) in ether (1.5 ml) and the reaction mixture is stirred for 7 hours at 50° C. (solution A).

Triphenylarsine (AsPh$_3$) (2.0 mg, 0.007 mmol) and the Pd$_2$(dba)$_3$ complex (6.0 mg, 0.007 mmol) are added to a solution of the iodide obtained in Example 1 (1e) (77 mg, 0.22 mmol) in anhydrous NMP (3 ml). After stirring for 10 minutes, the above solution A is then added and the reaction mixture is stirred for 8 hours at room temperature. After having added 3 ml of a saturated potassium fluoride solution, extraction is carried out with ether (3×7 ml) and the combined organic phases are dried over MgSO$_4$ and then evaporated. The residue is purified by silica chromatography, elution being carried out using a hexane/ethyl acetate (90/10) mixture, in order to result in 34 mg (46%) of the expected product in the form of a yellow solid.

$^1$H NMR (250.13 MHz, CDCl$_3$) δ 1.23 (s, 6H, 2×CH$_3$), 1.29 (s, 9H, t-Bu), 1.83 (t, J=6.9 Hz, 2H, 2H$_2$·), 2.28 (s, 3H, CH$_3$), 2.62 (t, J=6.9 Hz, 2H, 2H$_3$·), 5.22 (s, 1H, H$_1$), 5.48 (s, 1H, H$_7$), 5.62 (s, 1H, H$_7$), 5.89 (d, J=15.8 Hz, 1H, H$_4$), 6.78 (d, J=15.3 Hz, 1H, H$_5$), 6.95 (s, 1H, Ar—H), 7.70 (s, 1H, Ar—H) ppm;

$^{13}$C NMR (62.89 MHz CDCl$_3$) δ 13.7 (q), 28.5 (q, 2×), 28.6 (t), 31.5 (q, t-Bu), 34.5 (s), 41.4 (t), 44.0 (s), 118.0 (d), 119.3 (d), 120.5 (t), 124.0 (d), 134.9 (d), 135.1 (s), 135.9 (d), 137.8 (s), 147.8 (s), 149.7 (s), 152.6 (s), 152.7 (s), 167.7 (s), 171.8 (s) ppm;

MS (EI$^+$) m/e (relative intensity) 338 (M$^+$, 100), 323 (52), 249 (36), 234 (54), 233 (52), 181 (33), 179 (25), 165 (32), 131 (20), 128 (22), 103 (22), 91 (18), 77 (29), 57 (67);

HRMS (EI$^+$) calc.: for C$_{23}$H$_{30}$O$_2$ 338.2246, found: 338.2242;

FTIR (CHCl$_3$) ν 2953 (s, C—H), 2860 (m, C—H), 1683 (m, C=O), 1603 (s, C=C), 1451 (w), 1359 (w), 1248 (m), 1186 (m), 967 (w), 881 (w);

UV (CH$_3$OH) λ$_{max}$ (ε), 286 (15,700) nm.

Example 3

Methyl (2E,4E)-6-[4-(6-tert-butyl-1,1-dimethylindanyl)]hepta-2,4,6-trienoate (a) (2E,4E)-5-(tri-n-butylstannyl)penta-2,4-dien-1-ol CuCN (0.63 g, 7.06 mmol) is introduced into a round-bottomed flask placed under argon, THF (18 ml) is then added and the mixture is cooled to −78° C. n-Butyl-lithium (1.6 M, 8.8 ml, 14.01 mmol) is then added dropwise and the mixture is allowed to return slowly to room temperature. The mixture is again cooled to −78° C. and n-Bu$_3$SnH (3.8 ml, 14.01 mmol) is added, and the mixture is stirred for 10 minutes, during which the hydrogen is discharged. (2E)-Pent-2-en-4-yn-1-ol (0.50 g, 6.09 mmol) is then added and the reaction mixture is left stirring for 45 minutes before being poured into 200 ml of an iS NH$_4$OH/NH$_4$Cl (10/90) solution. Extraction is carried out with ether (3×100 ml), drying is carried out over Na$_2$SO$_4$ and evaporation is carried out under vacuum, in order to obtain, after silica chromatography, elution being carried out with a hexane/ethyl acetate/ triethylamine (89/10/1) mixture, 1.52 g of the expected product (67%) in the form of an oil.

$^1$H NMR (250.13 MHz, CDCl$_3$) δ 0.8–1.1 (m, 15H, n-Bu), 1.2–1.4 (m, 6H, n-Bu), 1.4–1.6 (m, 6H, n-Bu), 4.20 (br s, 2H, 2H$_1$), 5.79 (dt, J=15.6 and 5.8 Hz, 1H, H$_2$), 6.21 (dd, J=15.6 and 10.0 Hz, 1H, H$_3$), 6.26 (d, J=18.5 Hz, $^2$J$_{Sn-H}$=67.2 Hz, 1H, H$_5$), 6.54 (dd, J=18.5 and 10.0 Hz, $^3$J$_{Sn-H}$=59.2 Hz, 1H, H$_4$) ppm;

$^{13}$C NMR (62.89 MHz, CDCl$_3$) δ 9.6 (t, $^1$J$_{Sn-C}$=344.2/330.6 Hz, 3×), 13.8 (q, 3×), 27.4 (t, $^2$J$_{Sn-C}$=53.7 Hz, 3×), 29.3 (t, $^3$J$_{Sn-C}$=20.3 Hz, 3×), 63.5 (t, C$_1$), 131.0 (d), 134.9 (d, $^1$J$_{Sn-C}$=315.4 Hz, C$_5$), 135.4 (d), 146.2 (d) ppm;

MS (EI$^+$) m/e (relative intensity) 317 ([M-Bu+1]$^+$, 100), 315 (75), 313 (42), 261 (48), 259 (37), 257 (21), 251 (31), 249 (23), 247 (16), 205 (56), 203 (47), 201 (29), 137 (64), 135 (49), 133 (29), 121 (36), 119 (28), 117 (16);

HRMS (EI$^+$) calc.: for C$_{17}$H$_{35}$OSn 373.1704, found: 373.1693;

FTIR (CHCl$_3$) ν 3600–3200 (br, —OH), 2960 (s, C—H), 2925 (s, C—H), 2864 (s, C—H), 1579 (w, C=C), 1456 (mi C—O), 1006 (m) cm$^{-1}$.

(b) (2E,4E)-5-(tri-n-butylstannyl)penta-2,4-dienal

According to the same procedure as that described for the preparation of the compound of Example 1 (1b), a solution of the compound obtained in 3a above (500 mg, 1.34 mmol) and triethylamine (0.56 ml, 4.02 mmol) in CH$_2$Cl$_2$ (4.5 ml) is treated with sulphur trioxide-pyridine complex (640 mg, 4.02 mmol). After the same treatment, 348 mg (70%) of the expected compound are obtained in the form of an oil.

$^1$H NMR (250.13 MHz, CDCl$_3$) δ 0.8–1.2 (m, 15H, n-Bu), 1.2–1.4 (m, 6H, n-Bu), 1.4–1.6 (m, 6H, n-Bu), 6.06 (dd, J=15.0 and 8.0 Hz, 1H, H$_2$), 6.79 (dd, J=18.8 and 10.2 Hz, $^3$J$_{Sn-H}$=53.3 Hz, 1H, H$_4$), 7.00 (dd, J=15.3 and 10.2 Hz, H$_3$), 7.10 (d, J=18.8 Hz, $^2$J$_{Sn-H}$=60.7 Hz, 1H, H$_5$), 9.56 (d, J=8.0 Hz, 1H, CHO) ppm;

$^{13}$C NMR (62.89 MHz, CDCl$_3$) δ 9.6 (t, J$_{Sn-C}$=349.2/330.0 Hz, 3×), 13.6 (q, 3×), 27.2 (t, $^2$J$_{Sn-C}$=54.8 Hz, 3×), 29.0 (t, $^3$J$_{Sn-C}$=20.3 Hz, 3×), 130.1 (d), 144.3 (d), 151.5 (d, $^1$J$_{Sn-C}$=325.5/310.3 Hz, C$_5$), 153.6 (d, $^2$J$_{Sn-C}$=67.8 Hz, C$_4$), 194.5 (d, C$_1$) ppm;

MS (EI$^+$) m/e (relative intensity) 315 ([M-Bu+1]$^+$, 88), 314 (31), 313 (64), 312 (24), 311 (36), 259 (66), 258 (23), 257 (49), 256 (19), 255 (29), 203 ([M-Bu$_3$]$^+$, 100), 202 (38), 201 (84), 200 (33), 199 (52), 173 (26), 171 (19), 169 (10), 121 (47), 119 (39), 117 (23), 81 ([M-SnBu$_3$]$^+$, 76);

HRMS (EI$^+$) calc.: for C$_{17}$H$_{32}$OSn 372.1475, found: 372.1483.

(c) methyl (2E,4E)-5-(tri-n-butylstannyl)penta-2,4-dienoate

According to the same procedure as that described for the preparation of the compound of Example 1 (1c), a solution of the aldehyde obtained in 3b above (0.35 g, 0.94 mmol) in methanol (4.7 ml) is treated by adding a mixture of KCN (0.32 g, 4.93 mmol) and MnO$_2$ (1.63 g, 18.76 mmol). After the same treatment, 370 mg (98%) of the expected compound are isolated in the form of an oil.

$^1$H NMR (250.13 MHz, CDCl$_3$) δ 0.8–1.0 (m, 15H, n-Bu), 1.2–1.4 (m, 6H, n-Bu), 1.4–1.6 (m, 6H, n-Bu), 3.74 (s, 3H, CO$_2$CH$_3$), 5.80 (d, J=15.4 Hz, 1H, H$_2$), 6.64 (dd, J=18.7 and 9.9 Hz, $^3$J$_{Sn-H}$=54.3 Hz, 1H, H$_4$), 6.82 (d, J=18.7 Hz, $^2$J$_{Sn-H}$=63.2 Hz, 1H, H$_5$), 7.19 (dd, J=15.4 and 9.9 Hz, $^4$J$_{Sn-H}$=5.2 Hz, 1H, H$_3$) ppm;

$^{13}$C NMR (62.89 MHz, CDCl$_3$) δ 9.6 (t, $^1$J$_{Sn-C}$=347.8/335.1 Hz, 3×), 13.6 (q, 3×), 27.2 (t, $^2$J$_{Sn-C}$=54.4 Hz, 3×), 29.0 (t, $^3$J$_{Sn-C}$=20.4 Hz, 3×), 51.4 (q, CO$_2$CH$_3$), 119.4 (d), 144.2 (d), 146.7 (d, $^2$J$_{Sn-C}$=69.9 Hz, C$_4$), 147.5 (d, $^1$J$_{Sn-C}$=340.8/327.2 Hz, C$_5$), 167.9 (s, CO$_2$CH$_3$) ppm;

MS (EI$^+$) m/e (relative intensity) 345 ([M-Bu+1]$^+$, 100), 344 (36), 343 (73), 342 (28), 341 (41), 289 (53), 288 (18), 287 (40), 286 (15), 285 (23), 233 (76), 232 (24), 231 (61), 230 (21), 229 (36), 177 (13), 175 (10), 151 (41), 149 (32), 147 (21), 121 (18);

HRMS (EI$^+$) calc.: for C$_{18}$H$_{34}$O$_2$Sn 402.158, found: 402.1581;

FTIR (CHCl$_3$) ν 2956 (m, C—H), 2925 (m, C—H), 2853 (m, C—H), 1722 (s, C=O), 1626 (w, C=C), 1560 (w), 1435 (w), 1458 (w), 1439 (w), 1273 (m), 1213 (m), 1154 (m), 1101 (w), 1010 (w), 870 (w) cm$^{-1}$.

(d) methyl (2E,4E)-6-[4-(6-tert-butyl-1,1-dimethylindanyl)]hepta-2,4,6-trienoate Triphenylarsine (AsPh$_3$) (1.4 mg, 0.005 mmol) and the Pd$_2$(dba)$_3$ complex (4.1 mg, 0.005 mmol) are added to a solution of the iodinated derivative obtained in Example 1 (1e) (53 mg, 0.15 mmol) in anhydrous NMP (2.1 ml). After stirring for 10 minutes, a solution of the derivative obtained in 3c above (66 mg, 0.165 mmol) in NMP (1 ml) is added and then this solution is stirred at 60° C. for 1 hour. After having added 2 ml of a saturated potassium fluoride solution, the mixture is extracted with ether (3×5 ml) and the combined organic phases are washed with water (3×5 ml), dried over MgSO$_4$ and evaporated. The residue is purified by silica chromatography, elution being carried out using a hexane/ethyl acetate (95/5) mixture, in order to result in 42 mg (83%) of the expected compound in the form of a yellow solid.

$^1$H NMR (250.13 MHz, CDCl$_3$) δ 1.28 (s, 6H, 2×CH,), 1.33 (s, 9H, t-Bu), 1.87 (t, J=7.2 Hz, 2H, 2H$_2$), 2.66 (t, J=7.2 Hz, 2H, 2H$_3$), 3.73 (s, 3H, CO$_2$CH$_3$), 5.30 (s, 1H, H$_7$), 5.53 (s, 1H, H$_7$), 5.79 (d, J=15.3 Hz, 1H, H$_5$), 5.99 (dd, J=15.1 and 11.2 Hz, 1H, H$_4$), 6.77 (d, J=15.3 Hz, 1H, H$_2$), 7.00 (d, J=1.4 Hz, 1H, Ar—H), 7.14 (d, J=1.4 Hz, 1H, Ar—H), 7.37 (dd, J=15.2 and 11.2 Hz, 1H, H$_3$) ppm;

$^{13}$C NMR (62.89 MHz, CDCl$_3$) δ 28.6 (q, 2×), 28.7 (t), 31.6 (q, t-Bu), 34.6 (s), 41.5 (t), 44.1 (s), 51.4 (q), 118.2 (d), 121.0 (d), 121.5 (t), 124.0 (d), 129.3 (d), 134.9 (s), 137.9 (s), 142.1 (d), 144.7 (d), 147.6 (s), 149.8 (s), 152.7 (s), 167.5 (s) ppm;

MS (EI$^+$) m/e (relative intensity) 338 (M$^+$, 100), 323 ([M-CH$_3$]$^+$, 100), 291 (16), 249 (37), 237 (35), 235 (38), 207 (41), 193 (23), 191 (25), 179 (33), 178 (29), 167 (26), 165 (47), 152 (36), 57 (67);

HRMS (EI$^+$) calc.: for C$_{23}$H$_{30}$O$_2$ 338.2246, found: 338.2239;

FTIR (CHCl$_3$) ν 2950 (s, C—H), 2900 (m, C—H), 1716 (s, C=O), 1622 (s, C=C), 1449 (m), 1245 (s), 1147 (s), 1008 (m), 893 (w) cm$^{-1}$;

UV (CH$_3$OH)λ$_{max}$(ε), 206 (11,600) nm.

Example 4

(2E,4E)-6-[4-(6-tert-butyl-1,1-dimethyl-indanyl)]hepta-2,4,6-trienoic acid

A solution of the ester obtained in Example 3 above (24 mg, 0.07 mmol) in 0.2 ml of ether is added dropwise to a solution of KOSiMe$_3$ (90%, 10 mg, 0.07 mmol) in ether (0.5 ml) and the reaction mixture is stirred for 12 hours at 40° C. After having added 2 ml of water and stirred for 1 hour at room temperature, the pH of the solution is adjusted to 4–5 by addition of 0.1N HCl. The aqueous phase is extracted with ether (5×5 ml) and the combined organic phases are dried over MgSO$_4$, filtered and concentrated under vacuum. Purification by preparative silica thin layer chromatography using hexane/ethyl acetate (90/10) eluent results in 12 mg (52%) of the expected acid in the form of a yellow solid and in 4 mg (17%) of the starting material 3.

$^1$H NMR (250.13 MHz, CDCl$_3$) δ 1.28 (s, 6H, 2×CH$_3$), 1.34 (s, 9H, t-Bu), 1.88 (t, J=7.1 Hz, 2H, 2H$_2$), 2.67 (t, J=7.1 Hz, 2H, 2H$_3$), 5.34 (s, 1H, H$_7$), 5.57 (s, 1H, H$_7$), 5.78 (d, J=15.3 Hz, 1H, H$_5$) 6.01 (dd, J=15.3 and 11.4 Hz, 1H, H$_4$), 6.81 (d, J=15.3 Hz, 1H, H$_2$), 7.00 (s, 1H, Ar—H), 7.16 (s, 1H, Ar—H), 7.45 (dd, J=15.3 and 11.4 Hz, 1H, H$_3$) ppm;

$^{13}$C NMR (62.89 MHz, CDCl$_3$) δ 28.6 (q, 2×), 28.7 (t), 31.6 (q, t-Bu), 34.6 (s), 41.5 (t), 44.1 (s), 118.2 (d), 120.4 (d), 122.2 (t), 124.0 (d), 129.1 (d), 134.7 (s), 137.9 (s), 143.2 (d), 146.8 (d), 147.6 (s), 149.9 (s), 152.7 (s), 171.9 (s) ppm;

Ms (EI$^+$) m/e (relative intensity) 324 (M$^+$, 8), 271 (38), 269 (100), 268 (34), 267 (71), 265 (35), 213 (32), 211 (23), 177 (25), 155 (39), 153 (29), 58 (30), 57 (24);

HRMS (EI$^+$) calc.: for C$_{22}$H$_{28}$O$_2$ 324.2089, found: 324.2091;

FTIR (CHCl$_3$) ν 2955 (s, C—H), 2863 (m, C—H), 1687 (s, C=O), 1619 (s, C=C), 1459 (m), 1416 (m), 1363 (m), 1308 (m), 1272 (m), 1252 (m), 1146 (w), 1001 (m), 882 (m) cm$^{-1}$.

UV (CH$_3$OH)λ$_{max}$ (ε), 204 (44,646), 284 (34,921) nm.

Example 5

Methyl (2E,4E,6E)-7-[4-(6-tert-butyl-1,1-dimethylindanyl)]-3,7-dimethylhepta-2,4,6-trienoate (a) 6-tert-butyl-4-([E]-2-iodo-1-methylethen-1-yl)-1,1-dimethylindane AlMe$_3$ (0.4 ml, 4.12 mmol) is added at 0° C. to a suspension of Cp$_2$ZrCl$_2$ (bis(cyclopentadienyl)zirconium dichloride complex) (117 mg, 0.4 mmol) in CH$_2$Cl$_2$ (5.3 ml). The mixture is stirred at this temperature for 10 minutes and is then cooled to −23° C. Water (0.04 ml, 2.06 mmol) is then added with vigorous stirring, the mixture is stirred for an additional 10 minutes and then the alkyne obtained in Example 1 (1d) (300 mg, 1.33 mmol), in dichloromethane (2.10 ml), is added at −23° C. After having stirred for 30 minutes at this temperature, a solution of iodine (676 mg, 2.66 mmol) in THF (5.5 ml) is added dropwise at −50° C. The resulting mixture is then stirred for 5 hours at room temperature and then the reaction is halted by the addition of a THF/H$_2$O (1/1) mixture. Extraction is then carried out with hexane (3×15 ml) and washing is carried out with a solution of Na$_2$S$_2$O$_3$ (2×25 ml) in water (30 ml). The combined organic phases are dried over Na$_2$SO$_4$ and concentrated. Silica chromatography, elution being carried out with hexane, results in 439 mg of the expected compound (90%) in the form of a white solid.

$^1$H NMR (250.13 MHz, CDCl$_3$) δ 1.28 (s, 6H, 2×CH$_3$), 1.34 (s, 9H, t-Bu), 1.92 (t, J=7.1 Hz, 2H, 2H$_2$), 2.22 (d, J=1.1 Hz, 3H, 2H$_3$), 2.82 (t, J=7.1 Hz, 2H, 2H$_3$), 6.25 (br s, 1H, H$_2$), 7.03 (d, J=1.7 Hz, 1H, Ar—H), 7.13 (d, J=1.7 Hz, 1H, Ar—H) ppm;

$^{13}$C NMR (62.89 MHz, CDCl$_3$) δ 25.4 (q), 28.6 (q, 2×), 29.2 (t), 31.6 (q, t-Bu), 34.7 (s), 41.6 (t), 44.0 (s), 79.5 (d), 118 (d), 122.4 (d), 136.7 (s), 138.4 (s), 148.6 (s), 150.1 (s), 153.1 (s) ppm;

MS (EI$^+$) m/e (relative intensity) 368 (M$^+$, 44), 354 (21), 353 ([M—CH$_3$]$^+$, 100), 241 (14), 211 (15), 170 (13), 155 (9), 128 (6);

HRMS (EI$^+$) calc. for C$_{18}$H$_{25}$I 368.1002, found 368.0997;

FTIR (CHCl$_3$) μ2953 (s, C—H), 2863 (m, C—H), 1460 (m), 1363 (w), 1200 (w), 878 (w), 789 (w) cm$^{-1}$.

(b) methyl (2E,4E,6E)-7-[4-(6-tert-butyl-1,1-dimethyl-indanyl)]-3,7-dimethylhepta-2,4,6-trienoate Triphenylarsine (AsPh$_3$) (1.9 mg, 0.006 mmol) and Pd$_2$(dba)$_3$ complex (5.5 mg, 0.006 mmol) are added to a solution of the iodide obtained above in 5a (75 mg, 0.204 mmol) in anhydrous NMP (3 ml). After 10 minutes, a solution of the stannic derivative obtained in Example 1 (1c) (93 mg, 0.224 mmol) in NMP (1.5 ml) is added and the solution is stirred at room temperature for 12 hours. After addition of 4 ml of a saturated potassium fluoride solution, the mixture is extracted with ether (3×5 ml). The organic phases are combined, washed with water (3×5 ml), dried over MgSO$_4$ and evaporated. The residue is purified by flash silica chromatography, elution being carried out using a hexane/ethyl acetate (95/5) mixture, in order to result in 67 mg (90%) of the expected product in the form of a yellow solid, of melting point: 118° C.

$^1$H NMR (250.13 MHz, CDCl$_3$) δ 1.30 (s, 6H, 2×CH$_3$), 1.36 (s, 9H, t-Bu), 1.93 (t, J=7.1 Hz, 2H, 2H$_2$), 2.25 (s, 3H, CH$_3$), 2.42 (s, 3H, CH$_3$), 2.90 (t, J=7.1 Hz, 2H, 2H$_3$), 3.74 (s, 3H, CO$_2$CH$_3$), 5.83 (s, 1H, H$_2$), 6.28 (d, J=11.2 Hz, 1H, H$_6$), 6.33 (d, J=15.2 Hz, 1H, H$_4$), 7.04 (dd, J=15.2 and 11.2 Hz, 1H, H$_5$), 7.13 (s, 2H, 2×Ar—H) ppm;

$^{13}$C NMR (62.89 MHz, CDCl$_3$) δ 13.8 (q), 17.9 (q), 28.5 (q, 2×), 29.6 (t), 31.6 (q, t-Bu), 34.7 (s), 41.6 (t), 43.8 (s), 50.9 (q), 118.1 (d), 118.3 (d), 122.2 (d), 128.6 (d), 131.1 (d), 135.3 (d), 137.0 (s), 140.2 (s), 142.3 (s), 149.9 (s), 153.0 (s), 153.1 (s), 167.6 (s) ppm;

MS (EI⁺) m/e (relative intensity) 366 (M⁺, 31), 351 (8), 309 (38), 291 (14), 277 (22), 253 (16), 252 (34), 251 (36), 249 (49), 237 (25), 235 (26), 229 (28), 228 (23), 213 (17), 197 (59), 195 (29), 193 (21), 181 (28), 179 (18), 165 (26), 155 (24), 83 (16), 57 (t-Bu⁺, 100);

FTIR (CHCl$_3$) v2952 (s, C—H), 2865 (m, C—H), 1711 (s, C=O), 1600 (s, C=C), 1444 (m), 1361 (w), 1240 (m), 1155 (s), 963 (w), 879 (w), 754 (m) cm⁻¹;

UV (CH$_3$OH)$\lambda_{max}$ ($\epsilon$), 334 (21,100) nm.

Example 6

(2B,4E,6B)-7-[4-(6-tert-Butyl-1,1-dimethyl-indanyl)]-3,7-dimethylhepta-2,4,6-trienoic acid A solution of the ester obtained in Example 5 above (45 mg, 0.123 mmol) in 0.3 ml of ether is added dropwise with stirring to a solution of KOSiMe$_3$ (90%, 17 mg, 0.123 mmol) in ether (0.75 ml) and the reaction mixture is stirred for 12 h at 40° C. After addition of 2 ml of water and stirring for 1 hour at room temperature, the pH of the solution is adjusted to 4–5 by addition of 0.1N HCl. The aqueous phase is then extracted with ether and the combined organic phases are dried over MgSO$_4$, filtered and concentrated under vacuum. The residue is purified by flash silica chromatography using a hexane/ethyl acetate (80/20) eluent, in order to result in 37 mg (85%) of the expected acid in the form of a yellow solid, of melting point: 185–190° C.

¹H NMR (250.13 MHz, CDCl$_3$) δ 1.32 (s, 6H, 2×CH$_3$), 1.38 (s, 9H, t-Bu), 1.94 (t, J=7.0 Hz, 2H, 2H$_2'$), 2.28 (s, 3H, CH$_3$), 2.44 (s, 3H, CH$_3$), 2.92 (t, J=7.0 Hz, 2H, 2H$_3'$), 5,87 (s, 1H, H$_2$), 6.31 (d, J=11.7 Hz, 1H, H$_6$), 6.38 (d, J=15.4 Hz, 1H, H$_4$), 7.10 (dd, J=15.4 and 11.7 Hz, 1H, H$_5$), 7.15 (s, 2H, 2×Ar—H) ppm;

¹³C NMR (62.89 MHz, CDCl$_3$) δ 14.0 (q), 18.0 (q), 28.5 (q, 2×), 29.7 (t), 31.6 (q, t-Bu), 34.7 (s), 41.7 (t), 43.8 (s), 18.2 (d, 2×), 122.3 (d), 128.6 (d), 131.8 (d), 135.2 (d), 137.0 (s), 140.1 (s), 143.0 (s), 149.9 (s), 153.2 (s), 155.3 (s), 172.7 (s) ppm;

FTIR (CHCl$_3$) v3033 (w, C—H), 2959 (s, C—H), 2863 (m, C—H), 1715 (s, C=O), 1610 (s, C=C), 1568 (w), 1448 (m), 1308 (m), 1254 (m), 1140 (m), 1004 (m), 869 (w) cm⁻¹.

Example 7

Methyl (2E,4E,6E)-7-[4-(6-tert-butyl-1,1-dimethylindanyl)]-7-methylhepta-2,4,6-trienoate Triphenylarsine (1.9 mg, 0.006 mmol) and Pd$_2$(dba)$_3$ complex (5.5 mg, 0.006 mmol) are added to a solution of the iodide obtained in Example 5 (5a) (75 mg, 0.204 mmol) in anhydrous NMP (3 ml). After stirring for 10 minutes, a solution of the stannic derivative obtained in Example 3 (3c) (90 mg, 0.224 mmol) in NMP (1.5 ml) is added and the resulting mixture is stirred at room temperature for 5 hours. After addition of 4 ml of a saturated aqueous KF solution, the mixture is extracted with ether (3×5 ml) and the combined organic phases are washed with water (3×5 ml), dried over MgSO$_4$ and evaporated. The residue is purified by flash silica chromatography using a hexane/ethyl acetate (95/5) eluent, in order to result in 65 mg (90%) of the expected compound in the form of a yellow solid of melting point: 121° C.

¹H NMR (250.13 MHz, CDCl$_3$) δ 1.33 (s, 6H, 2×CH$_3$), 1.38 (s, 9H, t-Bu), 1.94 (t, J=7.1 Hz, 2H, 2H$_2'$), 2.26 (s, 3H, CH$_3$), 2.91 (t, J=7.1 Hz, 2H, 2H$_3'$), 3.79 (s, 3H, CO$_2$CH$_3$), 5.93 (d, J=15.3 Hz, 1H, H$_2$), 6.29 (d, J=11.4 Hz, 1H, H$_6$), 6.40 (dd, J=14.7 and 11.4 Hz, 1H, H$_4$), 7.01 (dd, J=14.7 and 11.4 Hz, 1H, H$_5$), 7.15 (br s, 2H, 2×Ar—H), 7.48 (dd, J=15.3 and 11.4 Hz, H$_3$) ppm;

¹³C NMR (62.89 MHz, CDCl$_3$) δ 17.9 (q), 28.5 (q, 2×), 29.6 (t), 31.5 (q, t-Bu), 34.6 (s), 41.6 (t), 43.8 (s), 51.3 (q), 118.2 (d), 119.6 (d), 122.2 (d), 128.3 (d), 129.6 (d), 136.9 (s), 137.3 (d), 139.9 (s), 143.6 (s), 145.2 (d), 149.9 (s), 153.1 (s), 167.6 (s) ppm;

FTIR (CHCl$_3$) v3026 (w, C—H), 2956 (s, C—H), 2865 (m, C—H), 1715 (s, C=O), 1606 (s, C=C), 1440 (m), 1359 (w), 1308 (m), 1252 (m), 1139 (m), 1001 (m), 881 (w) cm⁻¹.

Example 8

(2E,4E,6E)-7-[4-(6-tert-Butyl-1,1-dimethyl-indanyl)]-7-methylhepta-2,4,6-trienoic acid A solution of the ester obtained above in Example 7 (57 mg, 0.162 mmol) in 0.5 ml of ether is added dropwise with stirring to a solution of KOSiMe$_3$ (90%, 23 mg, 0.162 mmol) in ether (1 ml) and the reaction mixture is stirred for 12 h at 40° C. After addition of 2 ml of water and stirring for 1 hour at room temperature, the pH of the solution is adjusted to 4–5 by addition of 0.1N HCl. The aqueous phase is then extracted with ether (5×5 ml) and the combined organic phases are dried over MgSO$_4$, filtered and concentrated under vacuum. The residue is purified by flash silica chromatography using a hexane/ ethyl acetate (80/20) eluent, in order to result in 40 mg (73%) of the acid in the form of a yellow solid, of melting point: 196° C.

¹NMR (250.13 MHz, CDCl$_3$) δ 1.28 (s, 6H, 2×CH$_3$), 1.34 (s, 9H, t-Bu), 1.91 (t, J=7.0 Hz, 2H, 2H$_2'$), 2.24 (s, 3H, CH$_3$), 2.88 (t, J=7.0 Hz, 2H, 2H$_3'$), 5.90 (d, J=15.1 Hz, 1H, H$_2$), 6.28 (d, J=11.5 Hz, 1H, H$_6$), 6.40 (dd, J=14.2 and 11.5 Hz, 1H, H$_4$), 7.03 (dd, J=14.7 and 11.2 Hz, 1H, H$_5$), 7.12 (m, 2H, 2×Ar—H), 7.53 (dd, J=15.1 and 11.5 Hz, H$_3$) ppm;

¹³C NMR (62.89 MHz, CDCl$_3$) δ 18.0 (q), 28.5 (q, 2×), 29.7 (t), 31.6 (q, t-Bu), 34.7 (s), 41.7 (t), 43.8 (s), 118.3 (d), 119.2 (d), 122.2 (d), 128.3 (d), 129.4 (d), 136.3 (d), 137.0 (s), 138.3 (d), 139.9 (s), 147.3 (s), 149.9 (s), 153.2 (s), 172.4 (s) ppm;

FTIR (CHCl$_3$) v3051 (m, C—H), 2956 (s, C—H), 2857 (m, C—H), 1679 (s, C=O), 1592 (s, C=C), 1447 (m), 1259 (m), 1188 (m), 960 (w), 757 (w) cm⁻¹.

Example 9

In This Example, Various Pharmaceutical and Cosmetic Formulations Based on the Compounds According to the Invention Have Been illustrated A) Oral Route (a) The following composition is prepared in the form of an 0.8 g tablet

| | |
|---|---|
| Compound of Example 1 | 0.005 g |
| Pregelatinized starch | 0.265 g |
| Microcrystalline cellulose | 0.300 g |
| Lactose | 0.200 g |
| Magnesium stearate | 0.030 g |

For the treatment of acne, 1 to 3 tablets daily are administered to an adult for 3 to 6 months, depending on the seriousness of the case treated.

(b) A suspension to be taken orally, intended to be packaged in 5 ml phials, is prepared:

| | |
|---|---|
| Compound of Example 2 | 0.050 g |
| Glycerol | 0.500 g |
| 70% Sorbitol | 0.500 g |
| Sodium saccharinate | 0.010 g |
| Methyl para-hydroxybenzoate | 0.040 g |
| Flavouring agent | q.s. |
| Purified water | q.s. for 5 ml |

For the treatment of acne, 1 phial daily is administered to an adult for 3 months, depending on the seriousness of the case treated.

(c) The following formulation, intended to be packaged in hard gelatin capsules, is prepared:

| | |
|---|---|
| Compound of Example 4 | 0.025 g |
| Maize starch | 0.060 g |
| Lactose | q.s. for 0.300 g |

The hard gelatin capsules used are composed of gelatin, titanium dioxide and a preservative.

In the treatment of psoriasis, 1 hard gelatin capsule daily is administered to an adult for 30 days.

Example (d)

The following composition is prepared in the form of an 0.8 g tablet

| | |
|---|---|
| Compound of Example 10 | 0.005 g |
| Pregelatinized starch | 0.265 g |
| Microcrystalline cellulose | 0.300 g |
| Lactose | 0.200 g |
| Magnesium stearate | 0.030 g |

For the treatment of acne, 1 to 3 tablets daily are administered to an adult for 3 to 6 months, depending on the seriousness of the case treated.

B) Topical Route (a) A non-ionic water-in-oil cream is prepared by mixing the following ingredients:

| | |
|---|---|
| Compound of Example 4 | 0.100 g |
| Mixture of emulsifying lanolin alcohols and of refined waxes and oils, sold under the name "Anhydrous Eucerin" by the Company BDF | 39.900 g |
| Methyl para-hydroxybenzoate | 0.075 g |
| Propyl para-hydroxybenzoate | 0.075 g |

Sterile demineralized water . q.s. for 100.000 g

This cream is applied to a psoriatic skin 1 to 2 times daily for 30 days.

(b) A gel is prepared by mixing the following ingredients:

| | |
|---|---|
| Compound of Example 5 | 0.050 g |
| Erythromycin base | 4.000 g |
| Butylated hydroxytoluene | 0.050 g |
| Hydroxypropylcellulose, sold under the name of "Klucel HF" by the company Hercules | 2.000 g |
| Ethanol (95°) | q.s. for 100.000 g |

This gel is applied, to a skin affected by dermatosis or a skin affected by acne, 1 to 3 times daily for 6 to 12 weeks, depending on the seriousness of the case treated.

(c) An antiseborrhoeic lotion is prepared by mixing the following ingredients:

| | |
|---|---|
| Compound of Example 6 | 0.030 g |
| Propylene glycol | 5.000 g |
| Butylated hydroxytoluene | 0.100 g |
| Ethanol (95°) | q.s. for 100.000 g |

This lotion is applied twice daily to a seborrhoeic scalp and a significant improvement is observed over a period of between 2 and 6 weeks.

(d) A cosmetic composition against the harmful effects of the sun is prepared by mixing the following ingredients:

| | |
|---|---|
| Compound of Example 7 | 1.000 g |
| Benzylidenecamphor | 4.000 g |
| Fatty acid triglycerides | 31.000 g |
| Glycerol monostearate | 6.000 g |
| Stearic acid | 2.000 g |
| Cetyl alcohol | 1.200 g |
| Lanolin | 4.000 g |
| Preservatives | 0.300 g |
| Propylene glycol | 2.000 g |
| Triethanolamine | 0.500 g |
| Perfume | 0.400 g |
| Demineralized water | q.s. for 100.000 g |

This composition is applied daily and it makes it possible to combat photoinduced ageing.

(e) A non-ionic oil-in-water cream is prepared by mixing the following ingredients:

| | |
|---|---|
| Compound of Example 8 | 0.500 g |
| Vitamin $D_3$ | 0.020 g |
| Cetyl alcohol | 4.000 g |
| Glycerol monostearate | 2.500 g |
| Polyethylene glycol 50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water | q.s. for 100.000 g |

This cream is applied to a psoriatic skin 1 to 2 times daily for 30 days.

(f) A topical anti-acne gel is prepared by mixing the following ingredients:

| | |
|---|---|
| Compound of Example 4 | 0.100 g |
| Poloxamer 182 (Pluronic L 62) | 0.200 g |
| Propylene glycol | 4.000 g |
| Carboxyvinyl polymer, sold under the name of "Carbopol 940" by the Company "Goodrich" | 0.800 g |

-continued

| | |
|---|---|
| Ethylenediaminetetraacetic acid (EDTA), disodium salt | 0.100 g |
| Methyl para-hydroxybenzoate | 0.100 g |
| NaOH, 10% in water | 1.250 g |
| Sterile demineralized water | q.s. for 100.000 g |

This gel is applied in the treatment of acne 1 to 3 times daily for 6 to 12 weeks, depending on the seriousness of the case treated.

(g) A hair lotion for combating hair loss and for promoting hair growth is prepared by mixing the following ingredients:

| | |
|---|---|
| Compound of Example 3 | 0.05 g |
| Compound sold under the name of "Minoxidil" | 1.00 g |
| Propylene glycol | 20.00 g |
| Ethanol | 34.92 g |
| Polyethylene glycol (molecular mass = 400) | 40.00 g |
| Butylated hydroxyanisole | 0.01 g |
| Butylated hydroxytoluene | 0.02 g |
| Water | q.s. for 100.00 g |

This lotion is applied twice daily for 3 months to a scalp which has experienced significant hair loss.

(h) An anti-acne cream is prepared by mixing the following ingredients:

| | |
|---|---|
| Compound of Example 4 | 0.050 g |
| Retinoic acid | 0.010 g |
| Mixture of stearates of glycerol and of polyethylene glycol (75 mol), sold under the name of "Gelot 64" by the Company "Gattefosse" | 15.000 g |
| Kernel oil polyoxyethylenated with 6 mol of ethylene oxide, sold under the name of "Labrafil M2130 CS" by the Company "Gattefosse" | 8.000 g |
| Perhydrosqualene | 10.000 g |
| Preservatives | q.s. |
| Polyethylene glycol (molecular mass = 400) | 8.000 g |
| Ethylenediaminetetra-acetic acid (EDTA), disodium salt | 0.050 g |
| Purified water | q.s. for 100.000 g |

This cream is applied, to a skin affected by dermatosis or a skin affected by acne, 1 to 3 times daily for 6 to 12 weeks.

(i) An oil-in-water cream is prepared by mixing the following ingredients:

| | |
|---|---|
| Compound of Example 5 | 0.020 g |
| Betamethasone 17-valerate | 0.050 g |
| S-(Carboxymethyl)cysteine | 3.000 g |
| Polyoxyethylene (40 mol of ethylene oxide) stearate, sold under the name of "Myrj 52" by the Company "Atlas" | 4.000 g |
| Polyoxyethylenated sorbitan monolaurate containing 20 mol of ethylene oxide, sold under the name of "Tween 20" by the Company "Atlas" | 1.800 g |
| Mixture of glycerol mono- and di-stearate, sold under the name of "Géléol" by the Company "Gattefosse" | 4.200 g |
| Propylene glycol | 10.000 g |
| Butylated hydroxyanisole | 0.010 g |
| Butylated hydroxytoluene | 0.020 g |

-continued

| | |
|---|---|
| Cetyl/stearyl alcohol | 6.200 g |
| Preservatives | q.s. |
| Perhydrosqualene | 18.000 g |
| Mixture of caprylic/capric triglycerides sold under the name of "Miglyol 812" by the Company "Dynamit Nobel" | 4.000 g |
| Triethanolamine (99% by weight) | 2.500 g |
| Water | q.s. for 100.000 g |

This cream is applied twice daily for 30 days to a skin affected by dermatosis.

(j) A cream of oil-in-water type is prepared by mixing the following ingredients:

| | |
|---|---|
| Lactic acid | 5.000 g |
| Compound of Example 2 | 0.020 g |
| Polyoxyethylene (40 mol of ethylene oxide) stearate, sold under the name of "Myrj 52" by the Company "Atlas" | 4.000 g |
| Polyoxyethylenated sorbitan mono-laurate containing 20 mol of ethylene oxide, sold under the name of "Tween 20" by the Company "Atlas" | 1.800 g |
| Mixture of glycerol mono- and di-stearate, sold under the name of "Géléol" by the Company "Gattefosse" | 4.200 g |
| Propylene glycol | 10.000 g |
| Butylated hydroxyanisole | 0.010 g |
| Butylated hydroxytoluene | 0.020 g |
| Cetyl/stearyl alcohol | 6.200 g |
| Preservatives | q.s. |
| Perhydrosqualene | 18.000 g |
| Mixture of caprylic/capric tri-glycerides, sold under the name of "Miglyol 812" by the Company "Dynamit Nobel" | 4.000 g |
| Water | q.s. for 100.000 g |

This cream is applied once daily. It helps in combating ageing, whether photoinduced or chronologic.

Example (k)

A non-ionic oil-in-water cream is prepared by mixing the following ingredients:

| | |
|---|---|
| Compound of Example 12 | 0.500 g |
| Vitamin $D_3$ | 0.020 g |
| Cetyl alcohol | 4.000 g |
| Glycerol monostearate | 2.500 g |
| Polyethylene glycol 50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water q.s. for | 100.000 g |

This cream is applied to a psoriatic skin 1 to 2 times daily for 30 days.

Example (l)

An anti-acne cream is prepared by mixing the following ingredients:

| | |
|---|---|
| Compound of Example 14 | 0.050 g |
| Retinoic acid | 0.010 g |

| | |
|---|---|
| Mixture of stearates of glycerol and of polyethylene glycol (75 mol), sold under the name of "Gelot 64" by the Company "Gattefosse" | 15.000 g |
| Kernel oil polyoxyethylenated with 6 mol of ethylene oxide, sold under the name of "Labrafil M2130 CS" by the Company "Gattefosse" | 8.000 g |
| Perhydrosqualene | 10.000 g |
| Preservatives | q.s. |
| Polyethylene glycol (molecular mass = 400) | 8.000 g |
| Ethylenediaminetetra-acetic acid (EDTA), disodium salt | 0.050 g |
| Purified water q.s. for | 100.000 g |

This cream is applied. to a skin affected by dermatbsis or a skin affected by acne, 1 to 3 times daily for 6 to 12 weeks.

Example 9

3-[1-(6-tert-butyl-1,1-dimethylindan-4-yl)ethen-1-yl]-thiophene-2-carboxaldehyde Pd(PPh$_3$)4 (36 mg, 0.031 mmol) in DME:MeOH (3 ml, 2:1 v/v) was added to a solution of 6-tert-butyl-4-(1-iodoethen-1-yl)-1,1-dimethylindane obtained in Example 1 (le) (100 mg, 0.31 mmol) and the resulting solution was stirred for 15 min. 2-Carboxaldehyde-3-thiophene boronic acid (64 mg, 0.409 mmol) and an aqueous 2M Na$_2$CO$_3$ solution (0.49 ml, 0.975 mmol) were then sequentially added, and the resulting mixture was heated to 80° C. for 1 h. Upon cooling to 25° C., the mixture was filtered through Celite, and the solvent was removed under vacuum. The residue was purified by chromatography on silica gel (5:95 EtOAc/hexane) to provide 103 mg (97%) of the titled compound. m.p. 99–100° C. (EtOAc/hexane).

$^1$H-RMN (400.13MHz, CDCl$_3$): δ 1.24 (6H, s, C$_{1''}$-2CH$_3$), 1.33 (9H, s, C$_{6''}$-t-Bu), 1.81 (2H, t, J=7.1 Hz, 2H$_{2'}$), 2.45 (2H, t, J=7.1 Hz, 2H$_{3''}$), 5.56 (1H, d, J=1.2 Hz, H$_{2'}$), 5.69 (1H, s, d, J=1.2 Hz, H$_{2'}$), 7.02 (1H, d, J=5.0 Hz, ArH), 7.1–7.2 (2H, m, 2ArH), 7.63 (1H, d, J=5.0 Hz, ArH), 9.76 (1H, s, CHO), $^{13}$C-RMN (100.62 MHz, CDCl$_3$,): δ 28.6 (q, C$_{1''}$-2CH$_3$), 29.2 (t), 31.6 (q, C(CH$_3$)$_3$), 34.7 (s), 41.4 (t), 43.8 (s), 119.1 (d), 121.0 (t), 123.7 (d), 130.5 (d), 132.1 (s), 133.4 (d), 136,6 (s), 137,8 (s), 142.8 (s), 150.3 (s), 151.8 (s), 153.4 (s), 184.0 (d, C=O).

MS: m/z (%) 338 (M$^+$, 28), 309 (29), 282 (28), 267 (28), 253 (100).

HRMS: calc: for C$_{22}$H$_{26}$OS, 338.1704; found, 338.1703.

Example 10

3-[1-(6-tert-butyl-1,1-dimethylindan-4-yl)ethen-1-yl]-thiophene-2-carboxylic acid KCN (79 mg, 1.20 mmol), MnO$_2$, (407 mg, 1.20 mmol) and AcOH (0.04 ml) were sequentially added to a solution of the aldehyde obtained in Example 9 (79 mg, 0.23 mnol) in MeOH (2 ml). After stirring for 90 min, the reaction mixture was filtered through Celite (CH$_2$Cl$_2$, washing), and the resulting solution was extracted with a saturated aqueous NaHCO$_3$, solution, dried (Na$_2$SO$_4$), filtered, and the solvent was removed under vacuum. The residue was dissolved in EtOH (12 ml), 5N KOH (5 ml, 25.28 mmol) was added, and the mixture was heated to 80° C. for 30 min. Upon cooling to 25° C., water was added, the solution was acidified with HCl (10%, v:v), and extracted with Et$_2$O (3×25 ml), The combined organic extracts were dried (Na$_2$SO$_4$), filtered and evaporated to dryness. The residue was purified by chromatography on silica gel (30:70 EtOAc/hexane) to afford 75 mg (90%) of the titled compound. m.p. 146–148° C. (EtOAc/hexane).

$^1$H-RMN (400.13 MHz, CDCl$_3$): δ 1.22 (6H, s, C$_{1''}$-2CH$_3$), 1.30 (9H, s, C$_{6''}$-t-Bu), 1.80 (2H, t, J=7.1 Hz, 2H$_{2'}$), 2.51 (2H, t, J=7.1 Hz, 2H$_{3''}$), 5.50 (1H, d, J=1.2 Hz, H$_{2'}$), 5,58 (1H, s, d, J=1.2 Hz, H$_{2'}$), 6,98 (1H, d, J=5.0 Hz, ArH), 7.08 (1H, d, J=1.7 Hz, ArH), 7.09 (1H, d, J=1.7 Hz, ArH), 7.48 (1H, d, J=5.0 Hz, ArH).

$^{13}$C-RMN (100.62 MHz, CDCl$_3$,): δ 28.6 (q$_1$, Cl$_{1''}$ 2CH$_3$), 29.1 (t), 31.5 (q, C(CH$_3$)$_3$), 34.6 (s), 41.5 (t), 43.7 (s), 118.2 (d), 119.0 (t), 123.7 (d), 127.4 (s), 130.9 (d), 131.8 (d), 136.6 (s), 137.6 (s), 143.7 (s), 149,4 (s), 150.6 (s), 152.7 (s), 166.9 (s).

MS: m/z (%) 354 (M$^+$, 20), 309 (45), 265 (27), 253 (100).

HRMS: calc: for C$_{22}$H$_{26}$O$_2$S, 354.1653; found, 354.1346.

Example 11

2-[1-(6-tert-butyl-1,1-dimethylindan-4-yl)ethen-1-yl]-thiophene-3-carboxaldehyde Pd(PPh$_3$)$_4$ (36 mg, 0.031 mmol) in DME:MeOH (3 ml, 2:1 v/v) was added to a solution of the iodide as disclosed in Example 1 (e) (100 mg, 0.31 mnol) and the resulting solution was stirred for 15 min, 3-Carboxaldehyde-2-thiophene boronic acid (64 mg, 0.409 mmol) and an aqueous 2M Na$_2$CO$_3$ solution (0.49 ml, 0.975 mmol) were then sequentially added, and the resulting mixture was heated to 80° C. for 30 min. Upon cooling to 25° C., the mixture was filtered through Celite, and the solvent was removed under vacuum. The residue was purified by chromatography on silica gel (5:95 EtOAc/hexane) to provide 84 mg (80%) of the titled compound. m.p. 148–150° C. (EtOAc/hexane).

$^1$H-RMN (400.13 MHz, CDCl$_3$): δ 1.25 (6H, s, C$_{1''}$-2CH$_3$), 1.34 (9H, s, C$_{6''}$-t-Bu), 1.83 (2H, t, J=7.1 Hz, 2H2$_9$), 2.51 (2H, t, J=7.1 Hz, 2H$_{3''}$), 5.66 (2H, 2s, 2H$_{2'}$), 7.19 (1H, s, ArH), 7.20 (1H, s, ArH), 7.21 (1H, d, J=5.3 Hz, ArH), 7.49 (1H, d, J=5.3 Hz, ArH), 9.64 (1H, s, CHO).

$^{13}$C-RMN (100.62 MHz, CDCl$_3$): δ 28.5 (q, C$_{1''}$-2CH$_3$), 29.0 (t), 31.5 (q, C(CH$_3$)$_3$), 34.7 (s), 41.4 (t), 43.8 (s), 119.3 (d), 121.4 (t), 123.6 (d), (s), 124.8 (d), 126.4 (d), 136.9 (s), 137.8 (s), 138.3 (s), 140.8 (s), 150.4 (s), 153.5 (s), 156.6 (s), 185.5 (d).

MS: m/z (%) 338 (M$^+$, 30), 309 (30), 277 (50), 267 (28), 253 (100).

HRMS: calc: for C$_{22}$H$_{26}$OS, 338.1704; found, 338.1706.

Example 12

2-[1-(6-tert-butyl-1,1-dimethylindan-4-yl)ethen-1yl]-thiophene-3-carboxylic acid KCN (55 mg, 0.839 mmol), MnO$_2$ (283 mg, 3.25 mmol) and AcOH (0.03 ml) were sequentially added to a solution of the aldehyde obtained in Example 11 (55 mg, 0.163 mmol) in MeOH (1.5 ml). After stirring for 90 min at 25° C., the reaction mixture was filtered through Celite (CH$_2$Cl$_2$ washing), and the resulting solution was extracted with a saturated aqueous NaHCO$_3$ solution, dried (Na$_2$SO$_4$), filtered, and the solvent was removed under vacuum. The residue was dissolved in EtOH (8 ml), 5N KOH (3.54 ml, 17.69 mmol) was then added, and the mixture was heated to 80° C. for 30 min. Upon cooling to 25° C., water was added, the solution was acidified with HCl (10%, v:v), and the aqueous layer was extracted with Et$_2$O (3×20 ml,). The combined organic extracts were dried (Na$_2$SO$_4$), filtered and evaporated to dryness. The residue was purified by chromatography on silica gel (30:70 EtOAc/hexane) to provide 42 mg (74%) of the titled compound. m.p. 148–150° C. (EtOAc/hexane).

$^1$H-RMN (400.13 MHz, CDCl$_3$): δ 1.24 (6H, s, C$_{1''}$-2CH$_3$), 1.30 (9H, s, C$_{6''}$-t-Bu), 1.83 (2H, t, J=7.1 Hz, 2H$_{2''}$), 2.60 (2H, t, J=7.1 Hz, 2H$_{3''}$), 5.56 (1H, s, H$_{2'}$). 5.64 (1H, s, H$_{2'}$), 7.09 (1H, d. J=1.2 Hz, ArH), 7.10 (1H, J=1.2 Hz, ArH), 7.19 (1H, d, J=5.4 Hz, ArH), 7.41 (1H, d, J=5.4 Hz, ArH).

$^{13}$C-RMN (100.62 MHz, CDCl$_3$): δ 28.5 (q, C$_{1''}$-2CH$_3$), 29.0 (t), 31.5 (q, C(CH$_3$)$_3$), 34.5 (s), 41,6 (t.) 43.7 (s), 118.2 (d), 120.0 (t), 123.6 (d), 123.7 (d), 128.3 (s), 129.6 (d), 136.5 (s), 137.7 (s), 141.7 (s), 149.4 (s), 152.7 (s), 153.2 (s), 168.2 (s).

MS: m/z (%) 354 (M$^+$, 19), 309 (62), 265 (28), 253 (100).
HRMS: calc: for C$_{22}$H$_{26}$O$_2$S, 354.1654; found: 354.1657.

Example 13

Methyl 6-[(6-tert-butyl-1,1-dimethylindan-4-yl)ethen-1-yl]-3-pyridinecarboxylate a) Pinacol [(6-tert-butyl-1,1-dimethylindan-4-yl)ethen-1-yl] boronate t-BuLi (0.4 ml, 1.6 M in THF, 0.62 mmol) was added dropwise to a cooled (−78° C.) solution of the iodide as disclosed in Example 1 (e) (100 mg, 0.28 mnol) in THF (1 ml). After stirring the resulting solution for 30 min, B(OMe)$_3$ (0,16 ml, 1.41 mmol) was added, and the reaction mixture was slowly (ca. 1 h) allowed to reach 25° C. before pinacol (200 mg,1.58 mmol) was added, After stirring overnight, the solvent was removed under vacuum, and the residue was taken in CH$_2$Cl$_2$ and filtered through Celite (CH$_2$Cl$_2$ washing). The solvent was then removed, and the residue was purified by chromomatography on silica gel (98:2 CH$_2$Cl$_2$/Et$_3$N) to provide 48 mg (48%) of the titled compound, which was used without further purification.

$^1$H-RMN (400.13 MHz, CDCl$_3$): δ 1.24 (9H, s, C$_{1'}$-2CH$_3$), 1.26 (6H, s, C$_{6''}$-t-Bu), 1.32 (12H, s, 4×CH$_3$), 1.97 (2H, t, J=7.1 Hz, 2H$_{2'}$), 2.84 (2H, t, J=7.1 Hz, 2H$_3$), 5.91 (1H, d, J=3.4 Hz, H$_2$), 6.13 (1H, d, J=3.4 Hz, H$_2$), 7.08 (1H, J=1.2 Hz, ArH), 7.11 (1H, d, J=1.2 Hz, ArH).

b) Methyl 2-hydroxy-5-pyridinecarboxylate

Trimethylsilyldiazomethane (0.93 ml, 2.0 M in hexane, 1.87 mmol) was added to a suspension of 2-hydroxypyridine-5-carboxylic acid (200 mg, 1.44 mmol) in MeOH (2.8 ml) and benzene (10.0 ml) at 25° C. The resulting solution was stirred for 2 h and the solvent was removed to provide the corresponding methyl ester (209 mg, 95% yield) which was used in the next step without further purification.

$^1$H-RMN (400.13 MHz, CDCl$_3$): δ 3.87 (3H, s, OCH$_3$), 6.58 (1H, dd, J=9.4, 0.5 Hz, H$_3$), 8.00 (1H, dd, J=9.5, 2.4 Hz, H$_4$), 8.19 (1H, dd, J=2.4, 0.5 Hz, H$_5$).

c) Methyl 2-[(trifluoromethyl)-sulfonyloxy]-5-pyridinecarboxylate

Et$_3$N (0.09 ml, 0.646 mmol) was slowly added to a solution of the methyl ester, obtained above in (b), (94 mg, 0.615 mmol) and N-phenyltriflimide (200 mg, 0.615 mmol) in CH$_2$Cl$_2$ (2 ml), and the resulting mixture was stirred at 25° C. for 48 h. The reaction mixture was washed with a 1N aqueous NaOH solution (2×30 ml) and an aqueous Na$_2$CO$_3$ solution (2×30 ml), dried (Na$_2$SO$_4$), filtered, and the solvent was removed under vacuum. The residue was purified by chromatography on silica gel (99:1 CH$_2$Cl$_2$/MeOH) to afford 120 mg (68% yield) of the titled compound as an oil.

$^1$H- RMN (400.13 MHz, CDCl$_3$): δ 3.98 (3 H, s, O—CH$_3$), 7.25 (1H, d, J=8.5 Hz, H$_3$), 8.49 (1H, dd, J=8.5, 2.3 Hz, H$_4$), 9.01 (1H, d, J=2.3 Hz, H$_6$).

$^{13}$C-RMN (75.47 MHz, CDCl$_3$): δ 53.1 (q), 115.0 (d), 127.0 (s), 142.6 (d), 150.7 (d), 158,4 (s), 164.3 (s).

IR (CHCl$_3$): v3098 (w, C—H), 3094 (w, C—H), 3080 (m, C—H), 3060 (m, C—H), 1735 (s, C=O), 1584 (m), 1430 (s), 1285 (m), 1220 (s), 1130 (m), 920 (s) cm-'.

d) Methyl 6-(6-tert-butyl-1,1-dimethylindan-4-yl)ethen-1-yl]-3-pyridinecarboxylate Pd(PPh$_3$)$_4$ (30 mg, 0.025 mmol) was added to a solution or the compound obtained above in (c) (0.145 mg, 0.51 mmol) in DMF (3 ml), and the resulting solution was stirred at room temperature for 15 min. A solution of the pinacol boronate obtained above in (a) (200 mg, 0.56 mmol) in DMF (3 ml) was then added dropwise, followed by an 2M aqueous Na$_2$CO$_3$ solution (0.8 ml). The resulting mixture was heated to 90° C. for 12 h. Upon cooling down to 25° C., water was added, and the aqueous layer was extracted with EtOAc (2×30 ml). The combined organic layers were washed with a saturated aqueous NaHCO$_3$ solution, dried (Na$_2$SO$_4$) and evaporated to dryness. The residue was purified by chromatography on silica gel (CH$_2$Cl$_2$) to provide 160 mg (86%) of the titled product as an oil.

$^1$H-RMN (400.13 MHz, CDCl$_3$): δ 1.27 (6H, S, C$_{1''}$-2CH$_3$), 1.35 (9H, s, C$_{6''}$-t-Bu), 1.81 (2H, t, J=7.1 Hz, 2H$_{2''}$), 2.43 (2H, t, J=7.1 Hz, 2H$_{3''}$), 3.96 (3H, s, —OMe), 5.6 (1H, d, J=1.7 Hz, H$_{2'}$), 6.38 (1H, d, J=1.7 Hz, H$_{2'}$), 7.16 (1H, d, J=1.6 Hz, ArH), 7.18 (1H, d, J=8.2 Hz, ArH), 7.19 (1H, d, J=1.6 Hz, ArH), 8.18 (1H, dd, J=8.2, 2.2 Hz, ArH), 9.23 (1H, dd, J=2.2, 0.7 Hz, ArH).

$^{13}$CRMN (100.61 MHz, CD$_3$OD): δ 28.5 (q, C$_{1''}$-2CH$_3$), 28.9 (t), 31.5 (q, C(CH$_3$)$_3$), 34.6 (s), 41.4 (t), 43.9 (s), 52.1 (q, OMe), 118.5 (d), 120.6 (t), 121.4 (d), 124.1 (s), 124.4 (d), 135.5 (s), 137.4 (d), 138,1 (s), 148.1 (s), 149.9 (s), 150.5 (d), 152.6 (s), 161.4 (s), 165.7 (s).

IR (NaCl): v3020 (w, CH), 2956 (m, CH), 2927 (m, CH), 2857 (w, CH), 1723 (m, C=O), 1594 (w), 1295 (m), 1216 (s), 757 (s) cm$^{-1}$.

MS: m/z (%) 363 (M$^+$, 100), 348 (27), 339 (13), 306 (11), 292 (13).

HRMS: calc: for C$_{24}$H$_{29}$NO$_2$, 363.2198; found, 363.2205.

Example 14

6-[(6-tert-butyl-1,1-dimethylindan-4-yl)ethen-1-yl]-3-pyridinecarboxylic acid

A solution of the ester, obtained in Example 13, (20 mg, 0.055 mmol) in MeOH (3 ml) and 1N KOH (2 ml) was heated to 80° C. for 12 h. Upon cooling down to 25° C., the solution was acidified with HCl (10%, v/v) and extracted with EtOAc (2×15 ml). The combined organic layers were washed with H$_2$O (2×10 ml) and brine (2×10 ml), dried (Na$_2$SO$_4$) and evaporated to dryness. The residue was purified by chromatography on silica gel (20:80 EtOAc/hexane) to afford 16 mg (82%) of the titled compound as a thick oil.

$^1$H-RMN (400.13 MHz, CD$_3$OD): δ 1.22 (6H, s, C$_{1''}$-2CH$_3$), 1.32 (9H, s, C$_{6''}$-t-Bu), 1.76 (2H, t, J=7.1 Hz, 2H$_{2''}$), 2.34 (2H, t, J=7.1 Hz, 2H$_{3''}$), 5.49 (1H, s, H$_{2'}$), 6.08 (1H, s, H$_{2'}$), 7.12 (1H, d, J=1.5 Hz, ArH), 7.19 (2H, br s, 2ArH), 8.24 (1H, d, J=8.1 Hz, ArH), 9.06 (1H, br s, ArH).

$^{13}$C-RMN (100,61 MHz, CD$_3$OD): δ 27.9 (q, C$_{1''}$-2CH$_3$), 28.9 (t), 31.0 (q, C(CH$_3$)$_3$), 34.5 (s), 41.6 (t), 43.9 (s), 118.6 (t), 122.1 (d), 122.3 (s), 124.4 (d), 136.4 (d), 138.2 (d), 138.3 (s), 149.3 (s), 150.3 (d), 150.4 (s), 152.9 (s), 160.1 (s).

IR (NaCl), v3500–3190 (br, OH), 2955 (s, CH), 2863 (m, CH), 1596,(s, C=O), 1537 (m), 1414 (s), 758 (m) cm-$^1$.

MS: m/z (%) 350 (52), 349 (M$^+$, 100), 341 (17), 334 (28), 281 (35), 221 (32), 207 (11), 147 (35), 73 (55).

HRMS: calc: for C$_{23}$H$_{27}$NO$_2$, 349.2042; found, 349.2048.

TABLE 1

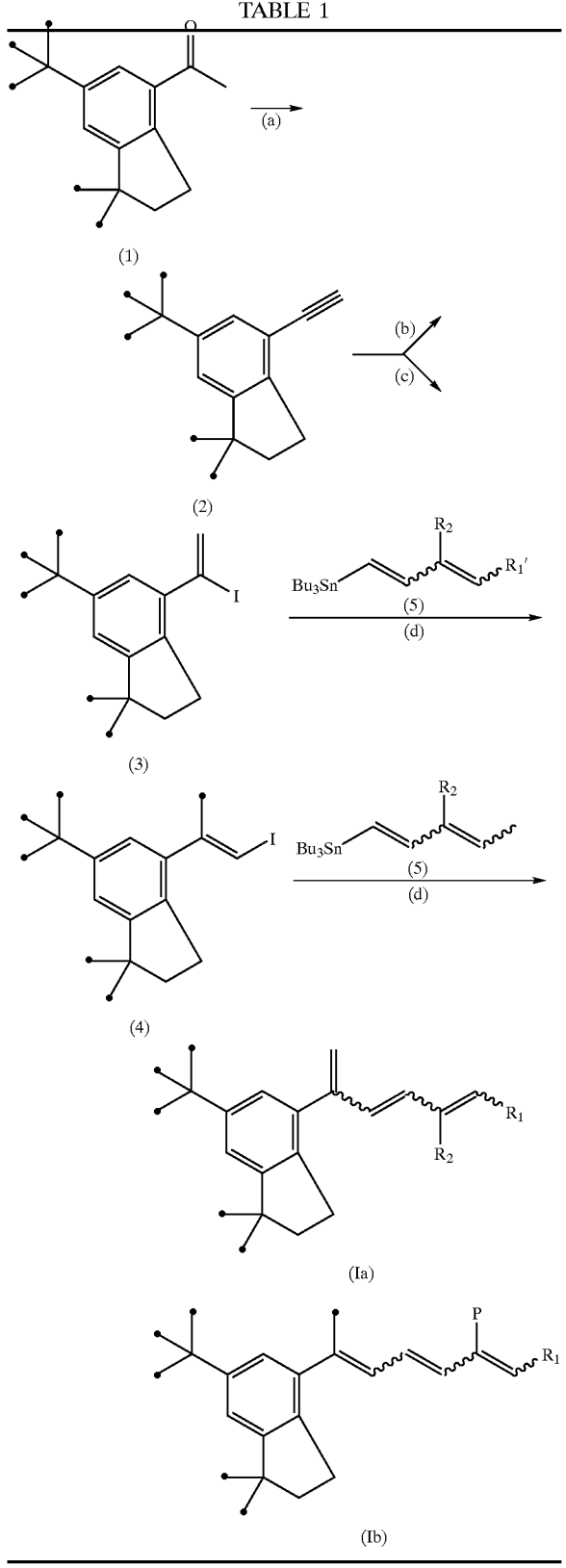

(a) 1/LDA, THF (−78° C.); 2/Cl(O) P(OEt)₂; 3/LDA, THF (−78° C.)
(b) NaI, Me₃SiCl, CH₃CN
(c) 1/Me₃Al, Cp₂ZrCl₂, H₂O, CH₂Cl₂ (−23° C.); 2/I₂, THF
(d) Pd₂(dba)₃, AsPh₃, NMP

TABLE 2

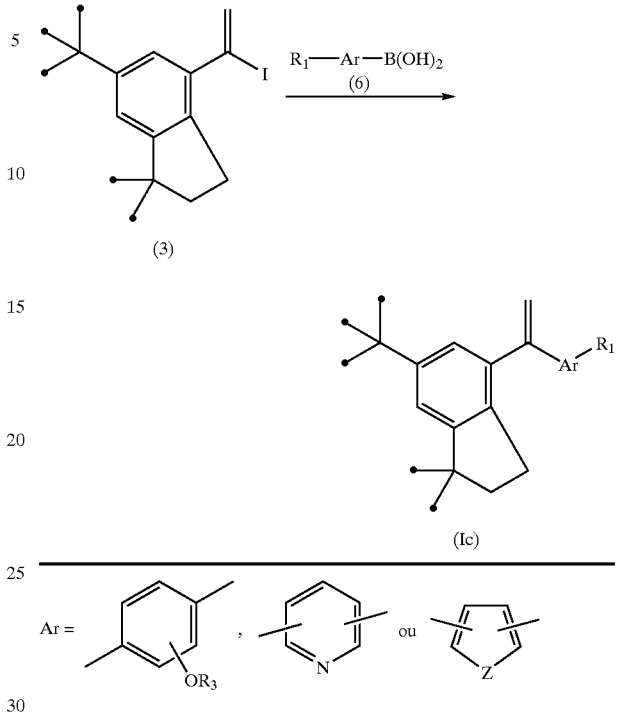

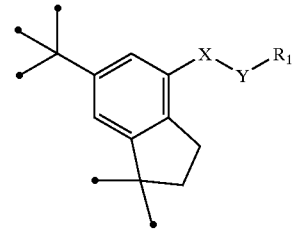

What is claimed is:

1. An unsaturated derivative at the 4-position of 6-tert-butyl-1,1-dimethylindane corresponding to the following formula:

(I)

in which:

X represents:
a divalent radical of formula:

 (c)

and Y then represents a divalent radicals of following formula:

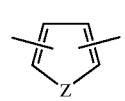 (f)

Z being —O—, —S— or $>$N—R₃
R₁ represents —CH₃, —(CH₂)$_p$—OR₄, —(CH₂)$_p$—COR₅ or —S(O)$_t$—R₈,
p being 0, 1, 2 or 3,
t being 0, 1 or 2, R4 represents H, lower alkyl, —COR₇, aryl, aralkyl, mono- or polyhydroxyalkyl, or a polyether radical, R₅ represents H, lower alkyl,

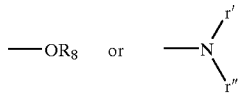

R₆ represents H or lower alkyl,

R₇ represents lower alkyl,

R₈ represents H, alkyl, alkenyl, alkynyl, aryl, aralkyl, mono- or polyhydroxyalkyl, a sugar residue selected from the group consisting of residues deriving from glucose, galactose, mannose and glucuronic acid or an amino acid residue deriving from lysine, glycine and aspartic acid, r' and r'', which are identical or different, represent H, lower alkyl, —COR₇, aryl, a sugar residue selected from the group consisting of residues deriving from glucose, galactose, mannose and glucuronic acid or an amino acid residue deriving from lysine, glycine and aspartic acid, or r' and r'', taken together, form a heterocycle selected from the group consisting of piperidino, morpholino, pyrrolidino and piperazino radical, the latter optionally being substituted in the 4-position by a $C_1$–$C_6$ alkyl radical or a mono- or polyhydroxyalkyl, and the salts of the compounds of formula (I), when $R_1$ represents a carboxylic acid functional group, and the geometrcal and optical isomers of the compounds of formula (I).

2. A derivative according to claim 1, provided in the form of a salt of an alkali metal or alkaline earth metal or alternatively of zinc or of an organic amine.

3. A derivative according to claim 1, wherein the lower alkyl radical is a linear or branched $C_1$–$C_6$ radical and is selected from the group consisting of metyl, ethyl, propyl, isopropyl, tert-butyl and n-hexyl radicals.

4. A derivative according to claim 1, wherein the alkyl radical is a linear or branched $C_1$–$C_{20}$ radical selected from the group consisting of methyl, ethyl, isopropyl, butyl, tert-butyl, 2-ethylhexyl, octyl, dodecyl, hexadecyl and octadecyl radicals.

5. A derivative according to claim 1, wherein the alkenyl radical is a $C_2$–$C_5$ radical exhibiting one or two ethylenic unsaturation(s).

6. A derivative according to claim 1, wherein the alkynyl radical is a $C_3$–$C_6$ radical selected from the group consisting of 2-propynyl, 2-butynyl and 2,4-hexadlynyl radical.

7. A derivative according to claim 1, wherein the acyl radical of formula —COR₇, wherein R₇ is lower alkyl, is selected from the group consisting of acetyl, propionyl and pivaloyl radical.

8. A derivative according to claim 1, wherein the monohydroxyalkyl radical is selected from the group consisting of 1-hydroxyethyl, 2-hydroxypropyl, 3-hydroxypropyl and 4-hydroxybutyl radical.

9. A derivative according to claim 1, wherein the polyhydroxyalkyl radical is selected from the group consisting of 2,3-dihydroxypropyl, 2,3,4-trihydroxybutyl, 2,3,4,5-tetrahydroxypentyl radical and the pentaerythritol residue.

10. A derivative according to claim 1, wherein the polyether radical is selected from the group consisting of methoxymethyl ether, methoxyethoxymethyl ether and methylthiomethyl ether radical.

11. A derivative according to claim 1, wherein the aryl radical is a phenyl radical optionally substituted by at least one halogen atom, hydroxyl group, nitro group, methoxy group and optionally substituted amine group.

12. A derivative according to claim 1, wherein the aralkyl radical is benzyl or phenethyl, optionally substituted by at least one halogen atom, hydroxyl, nitro or methoxy group.

13. A derivative according to claim 1, which corresponds to the following formula (II):

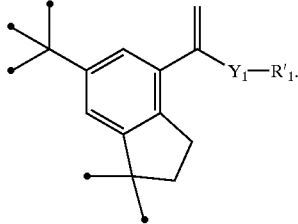

(II)

in which;

Y₁ represents the divalent radical of formula:

(f)

R'₁ represents —(CH₂)$_p$—COR'₅ p' being 0, 1, 2 or 3

R'₅ representing H, lower alkyl, —OR'₈ or

R'₈ being H or alkyl, and r' and r'', identical or different, being H or lower alkyl, and Z represents —O— or —S—, and the salts of the above compounds when R'₁ is a carboxylic acid functional group.

14. The derivative according to claim 1, which are selected from the group consisting of:

3-[1-(6-tert-butyl-1,1-dimethylindan-4-yl)ethen-1-yl]-thiophene-2-carboxylic acid, 3-[1-(6-tert-butyl-1,1-dimethylindan-4-yl)ethen-1-yl]-thiophene-2-carboxaldehyde, 2-[1-(6-tert-butyl-1,1-dimethylindan-4-yl)ethen-1-yl]-thiophene-3-carboxaldehyde, and 2-[1-(6-tert-butyl-1,1-dimethylindan-4-yl)ethen-1-yl]-thiophene-3-carboxylic acid.

15. A medicament comprising a derivative according to claim 1 in the form of a tablet, hard gelatin capsule, syrup, suspension, solution, powder, granule, emulsion or polymeric or lipid vesicle or nanosphere or microsphere.

16. The medicament according to claim 15 for treatment of dermatological conditions, dermatological conditions with an inflammatory and/or immunoallergic component of the rheumatic or respiratory type, or cardiovascular and ophthalmological conditions.

17. A pharmaceutical composition, comprising in a pharmaceutically acceptable vehicle, at least one derivative as defined according to claim 1.

18. The composition according claim 17, wherein the concentration of the derivative is between 0.001% and 5% by weight with respect to the total weight of the composition.

19. A cosmetic composition, comprising in a cosmetically acceptable vehicle, at least one derivative as defined according to claim 1.

20. The composition according to claim 19, wherein the concentration of the derivative is between 0.001 and 3% by weight with respect to the total weight of the composition.

21. The derivative according to claim 1, which corresponds to the following formula (II):

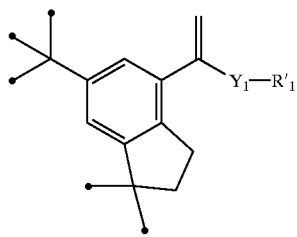 (II)
in which:
$Y_1$ represents the divalent radical of formula:
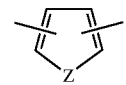 (f)
$R'_1$, represents $-(CH_2)_{p'}-COOR_8'$, p' is 0 and $R'_8$ representing H or lower alkyl.
* * * * *